US012691421B2

(12) United States Patent
Torres et al.

(10) Patent No.: US 12,691,421 B2
(45) Date of Patent: Jul. 28, 2026

(54) FILTER HOLDER FOR EXTRUSION OF LIPOSOMES

(71) Applicant: EVONIK OPERATIONS GMBH, Essen (DE)

(72) Inventors: Alex Torres, Vancouver (CA); David Jung, Surrey (CA); Norbert Maurer, Vancouver (CA)

(73) Assignee: Evonik Operations GmbH, Essen (DE)

( * ) Notice: Subject to any disclaimer, the term of this patent is extended or adjusted under 35 U.S.C. 154(b) by 856 days.

(21) Appl. No.: 17/918,849

(22) PCT Filed: Apr. 15, 2021

(86) PCT No.: PCT/CA2021/050505

§ 371 (c)(1),
(2) Date: Oct. 13, 2022

(87) PCT Pub. No.: WO2021/207841

PCT Pub. Date: Oct. 21, 2021

(65) Prior Publication Data

US 2023/0138197 A1 May 4, 2023

Related U.S. Application Data

(60) Provisional application No. 63/011,727, filed on Apr. 17, 2020.

(51) Int. Cl.
*B01D 69/10* (2006.01)
*A61K 9/1277* (2025.01)
(Continued)

(52) U.S. Cl.
CPC ............ *B01D 69/10* (2013.01); *A61K 9/1277* (2013.01); *B01D 61/147* (2013.01);
(Continued)

(58) Field of Classification Search
CPC ...... B01D 25/00; B01D 25/002; B01D 25/21; B01D 25/215; B01D 25/22; B01D 35/00;
(Continued)

(56) References Cited

U.S. PATENT DOCUMENTS

| 3,817,377 A | * | 6/1974 | Piggott | ............... B01D 29/945 |
| | | | | 425/197 |
| 5,626,751 A | * | 5/1997 | Kikuchi | ............... B01D 61/147 |
| | | | | 210/321.75 |
| 6,623,671 B2 | | 9/2003 | Coe et al. | |

OTHER PUBLICATIONS

PCT International Search Report and The Written Opinion of the International Searching Authority mailed Jul. 5, 2021 corresponding to PCT Application No. PCT/CA2021/050505 filed Apr. 15, 2021 (7 pages).

* cited by examiner

*Primary Examiner* — Allison G Fitzsimmons
(74) *Attorney, Agent, or Firm* — Linda S. Li; Jason S. Ngui; Andrew H. Chung

(57) ABSTRACT

A filter holder for liposome extrusion includes a housing having an inlet configured to receive a material to be extruded and an outlet, and a filter support member disposed within the housing between the inlet and the outlet. The filter support member includes an upstream side having a filter support surface configured to support a membrane filter assembly, a downstream side opposite the upstream side, and a plurality of passages extending through the filter support member from the filter support surface to the downstream side. The filter holder also includes an outlet cavity in fluid communication with the outlet, and the filter holder is configured such that the material to be extruded flows through the membrane filter assembly and into the outlet cavity via the plurality of passages before being discharged through the outlet.

21 Claims, 14 Drawing Sheets

(51) Int. Cl.
  B01D 61/14        (2006.01)
  B01D 63/08        (2006.01)
  B01D 69/06        (2006.01)
  *B01D 29/11*          (2006.01)

(52) U.S. Cl.
  CPC ......... B01D 63/087 (2013.01); B01D 63/088
        (2013.01); B01D 69/06 (2013.01); *B01D*
        *2311/103* (2013.01); *B01D 2311/106*
        (2013.01); *B01D 2313/041* (2022.08); *B01D*
        *2313/06* (2013.01); *B01D 2313/19* (2013.01);
        *B01D 2313/221* (2022.08); *B01D 2325/02834*
        (2022.08)

(58) Field of Classification Search
  CPC ...... B01D 35/02; B01D 35/30; B01D 35/301;
        B01D 35/306; B01D 2201/0407; B01D
        2201/0415; B01D 2201/043; B01D
        2201/30; B01D 2201/301; B01D 2313/20;
        B01D 2313/201; B01D 29/05; B01D
        33/0183; B01D 69/10
  See application file for complete search history.

FILTER HOLDER FOR EXTRUSION OF LIPOSOMES

This Application is a 35 U.S.C. § 371 U.S. national stage of PCT International Application No. PCT/CA2021/050505, filed Apr. 15, 2021, which claims the benefit of U.S. Provisional Patent Application No. 63/011,727 filed Apr. 17, 2020, the contents of each of which are hereby incorporated by reference in their entirety into this application.

FIELD OF THE DISCLOSURE

The present disclosure relates to filter holders for extrusion, and more particularly to filter holders for extrusion of liposomes.

BACKGROUND

Liposome extruders can be used to produce lipid vesicles (or liposomes) that are small and homogenous in size. For example, liposomes are most commonly made in a two-step process. First, a crude lipid or liposome suspension is formed comprising large heterogenous populations of liposomes. Subsequently, a liposome extruder may be used to reduce the size to produce smaller liposomes of defined size with homogenous size distribution by forcing the aqueous suspension of lipid through membrane filters with a defined uniform pore size. Such liposomes can be used in pharmaceutical, diagnostic, cosmetic and nutraceutical products, among others, as carriers of therapeutic, diagnostic, cosmetic or nutraceutical agents. However, existing liposome extruders have several drawbacks. First, the pores in the membrane filters tend to clog, particularly when processing large volumes, which is required for large-scale, commercial manufacturing of liposome products and when working with concentrated lipid suspensions required to maximize the amount of an agent (e.g. a therapeutic or diagnostic agent) that can be formulated in a liposome carrier. Replacing each clogged membrane filter opens the extruder to the environment and can pose a risk of product contamination and a risk of exposure of personnel and manufacturing facility to potentially hazardous agents (e.g. cytotoxic drugs, which are commonly formulated in a liposome carrier using an extrusion process). Thus, overcoming a fouled or clogged membrane filter adds time and expense to the extrusion process and may compromise the quality of the product.

The shortcomings of currently available liposome extruders are particularly acute when certain types of lipids are extruded. Lipid bilayers adopt a "rigid" gel phase below Tc, the so-called gel-to-liquid crystalline phase transition temperature, and a "fluid" liquid crystalline state above Tc. Lipids with Tc values greater than about room temperature can be especially difficult to extrude through membrane filters and require heating of the suspension above Tc. The value of Tc for a particular lipid depends on a number of factors, including the length and degree of saturation of the lipid's hydrocarbon chains. Lipids with longer, more saturated hydrocarbon chains (so-called gel state lipids) tend to have higher Tc values, above room temperature (and so tend to be more difficult to extrude through membrane filters) than lipids with shorter, less saturated hydrocarbon chains. Liposomes composed of gel state lipids are a preferred drug carrier system for intravenous administration of a wide variety of therapeutic agents. Commonly used gel phase lipids in liposome drug products such as hydrogenated soy phosphatidylcholine (HSPC) and distearoylphosphatidylcholine (DSPC) have Tc values above 50° C. and require heating to 60-65° C. (at least 10° C. above the Tc) for extrusion. As explained above, clogged or fouled membranes must be replaced, increasing cost of production and processing time. The latter in turn can impact product quality, as prolonged exposure to high temperature increases the potential for degradation of temperature-sensitive materials (lipids and agents associated with the liposomes).

The problem of clogged membrane filters is exacerbated by the filter support structures in existing extruders. An example of an existing filter holder 10 for liposome extrusion is illustrated in FIG. 1. The filter holder 10 includes a top housing plate (or inlet plate) and a bottom housing plate (or outlet plate) and a flat filter support disc 14 with a plurality of passages 18 extending through the filter support disc 14. The filter support disc 14 is positioned in a recess 22 of the bottom housing plate 26. The recess 22 includes radially-extending channels 30 that extend from and communicate with a central outlet opening 34.

Existing filter holders, such as the filter holder 10 illustrated in FIG. 1, limit the effective area of the membrane filter that is utilized. For example, referring to FIG. 2, the material to be extruded flows only through pores in the membrane filter proximate passages 18A in the filter support disc 14 that are aligned with the channels 30. There is little to no flow through pores in the membrane filter proximate passages 18B that do not line up with the channels 30. The material has no flow through the rest of the surface where the support plate rests flat on the bottom housing plate. Thus, only a small portion of the total area of the membrane filter is actually utilized during extrusion. This accelerates fouling (formation of deposits of material on the filter and rapid pressure build-up) and clogging of the membrane filter and requires frequent filter changes. In addition, the limited effective area results in lower throughput and higher extrusion pressures. As indicated above, all this increases processing time and may impact product quality. To decrease filter clogging and increase throughput and product quality it is important to increase/maximize surface area utilization.

SUMMARY

The present disclosure provides, in one aspect, a filter holder for liposome extrusion including a housing having an inlet configured to receive a material to be extruded and an outlet, and a filter support member disposed within the housing between the inlet and the outlet. The filter support member includes an upstream side having a filter support surface configured to support a membrane filter assembly, a downstream side opposite the upstream side, and a plurality of passages extending through the filter support member from the filter support surface to the downstream side. The filter holder also includes an outlet cavity in fluid communication with the outlet, and the filter holder is configured such that the material to be extruded flows through the membrane filter assembly and into the outlet cavity via the plurality of passages before being discharged through the outlet.

The present disclosure provides, in another aspect, a filter holder for liposome extrusion. The filter holder includes a housing defining a longitudinal center axis, the housing including an inlet extending from an inlet cavity and an outlet extending from an outlet cavity, and a filter support member disposed within the housing between the inlet cavity and the outlet cavity. The filter support member includes an upstream side adjacent the inlet cavity, the upstream side having a filter support surface configured to support a membrane filter assembly, a downstream side adjacent the outlet cavity and opposite the upstream side, and a plurality of passages extending through the filter support member from the upstream side to the downstream side. The filter holder is configured such that the material to be extruded flows through the membrane filter assembly and into the outlet cavity via the plurality of passages before being discharged through the outlet.

The present disclosure provides, in another aspect, an extrusion system including a supply reservoir containing material to be extruded, a pressure source configured to pressurize material to be extruded drawn from the reservoir, and a filter holder. The filter holder includes a housing having an inlet configured to receive the pressurized material to be extruded and an outlet configured to discharge an extrudate, a membrane filter assembly disposed between the inlet and the outlet, and a filter support member disposed within the housing. The filter support member includes an upstream side having a filter support surface configured to support the membrane filter assembly, a downstream side opposite the upstream side, the downstream side including a first recess, and a plurality of passages extending through the filter support member from the filter support surface to the first recess. The filter holder further includes an outlet cavity at least partially defined by the first recess. The outlet cavity is in fluid communication with the outlet. The extrusion system also includes a collection reservoir configured to receive the extrudate from the outlet of the filter holder.

In some embodiments, several filter holders can be combined in parallel to increase the throughput. One or more heat exchangers can be included to help maintain and control product temperature if heating of the product is required. Multiple extrusion passes can be performed by cycling the product from supply to collection vessel and back.

Other features and aspects of the disclosure will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

Figure 3:
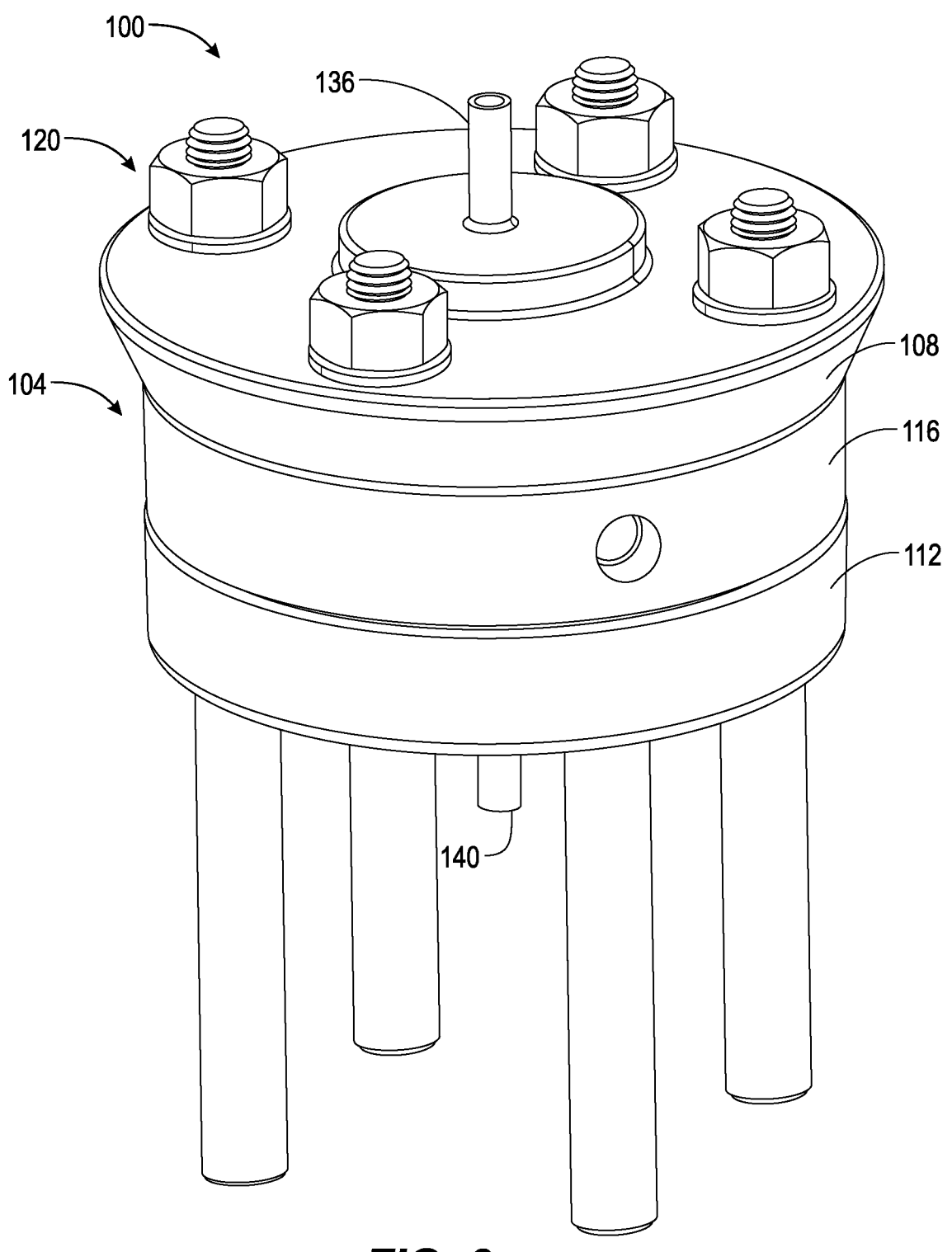
FIG. 3 is a perspective view of a filter holder according to an embodiment of the present disclosure.
Figure 4:
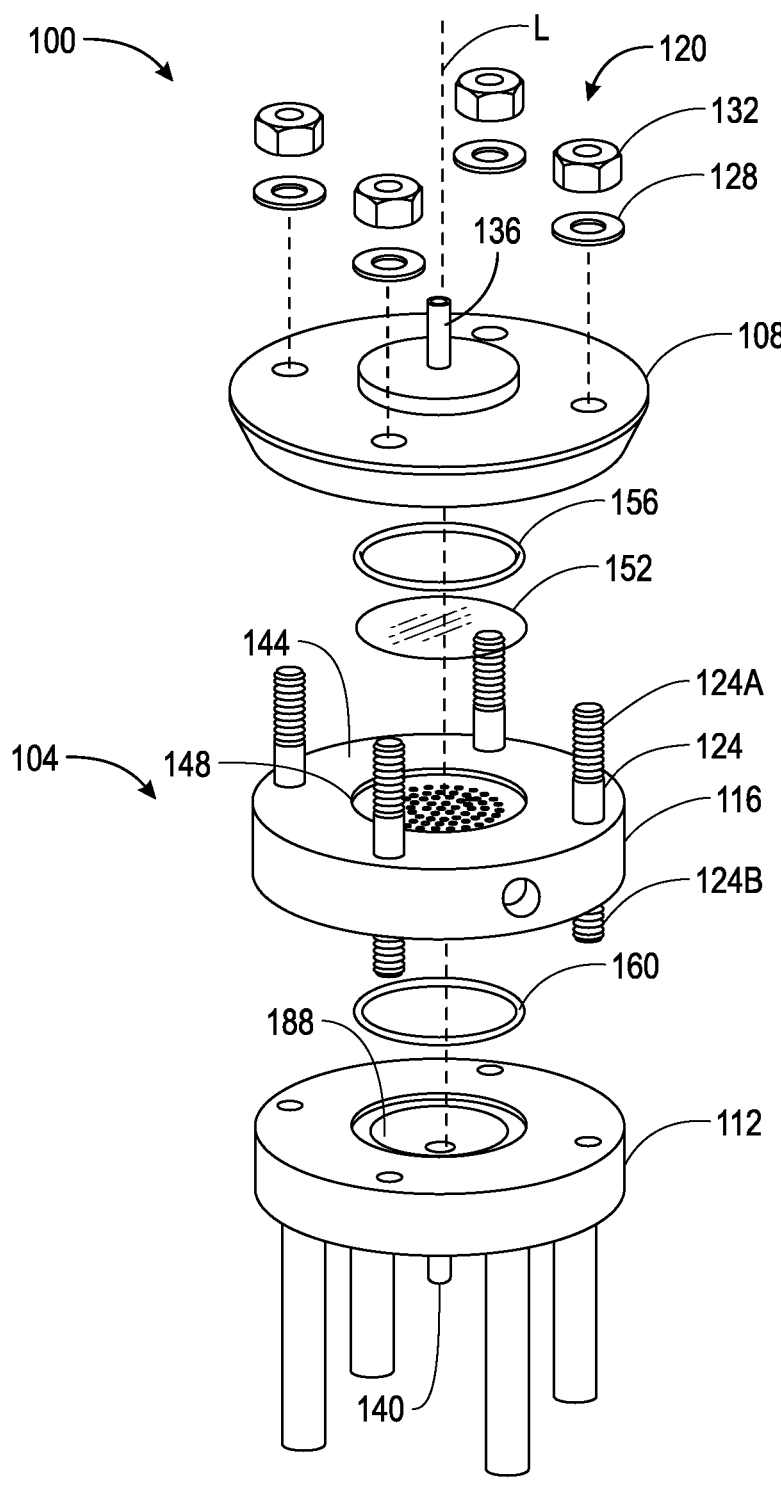
FIG. 4 is an exploded view of the filter holder of FIG. 3.

FIG. 3 illustrates a filter holder 100 according to an exemplary embodiment of the present disclosure. The filter holder 100 may be configured for use with a liposome extruder, such as a LIPEX® Extruder, or other small-pore extruders that may be employed in industries such as pharmaceutical, nutraceutical, biotechnology, cosmetic industries. The filter holder 100 includes a housing 104, which, in the illustrated embodiment, includes a first or upper housing portion 108, a second or lower housing portion 112, and a third or middle housing portion 116 positioned between the upper housing portion 108 and the lower housing portion 112. The housing 104 is generally cylindrical in the illustrated embodiment, extending along a central longitudinal axis L (FIG. 4). In other embodiments, the housing 104 may have other shapes, and the housing 104 may include any number of housing portions.

Referring to FIG. 4, the housing portions 108, 112, 116 are coupled together by a plurality of fastener assemblies 120 (e.g., four fastener assemblies 120 in the illustrated embodiment). Each of the fastener assemblies 120 includes a post 124, a washer 128, and a nut 132. The posts 124 extend from the lower housing portion 112 and through the middle and upper housing portions 116, 108. Each of the posts 124 has a first threaded end 124A and a second threaded end 124B opposite the first threaded end 124A. The nuts 132 are in threaded engagement with the first threaded ends 124A ends of the posts 124, and the washers 128 are positioned between the nuts 132 and the upper housing portion 108. The second threaded ends 124B of the posts 124 are threaded into the lower housing portion 112. The nuts 132 may thus be tightened to clamp the housing portions 108, 112, 116 together or loosened and/or removed from the posts 124 to permit disassembly of the housing 104 (e.g., for maintenance, changing filters, etc.). In other embodiments, the housing portions 108, 112, 116 may be secured together using other types and/or arrangements of fastener assemblies, threaded connections, tri-clamp connections, or any other suitable arrangement.

With reference to FIGS. 3 and 4, the filter holder 100 includes an inlet 136 for receiving a material to be extruded (e.g., an aqueous suspension containing large liposomes, which are heterogenous in size) and an outlet 140 for discharging extrudate (e.g., liposomes that are smaller in size and more homogeneous in size than the liposomes before extrusion). In the illustrated embodiment, the inlet 136 is provided on the upper housing portion 108, and the outlet 140 is provided on the lower housing portion 112. The inlet 136 may include a tube or sanitary tri-clamp connection, a threaded hole or post, or any other suitable interface for receiving the material to be extruded from a source, such as a pump or pressure vessel. The inlet 136 may have a nominal outer diameter between about 0.25 inches and about 1.0 inches in some embodiments, or the inlet 136 may have other nominal outer diameters, such as between about 0.25 inches and about 2.5 inches, between about 0.25 inches and about 5.0 inches, etc. Similarly, the outlet 140 may include a tube or sanitary tri-clamp connection, a threaded hole or post, or any other suitable interface for connecting to a downstream reservoir or the like configured to receive the extrudate that exits the filter holder 100. The outlet 140 may have a nominal outer diameter between about 0.25 inches and about 1.0 inches in some embodiments, or the outlet 140 may have other nominal outer diameters outside this range. The inlet 136 and the outlet 140 may have the same or different diameters in some embodiments.

Figure 5:
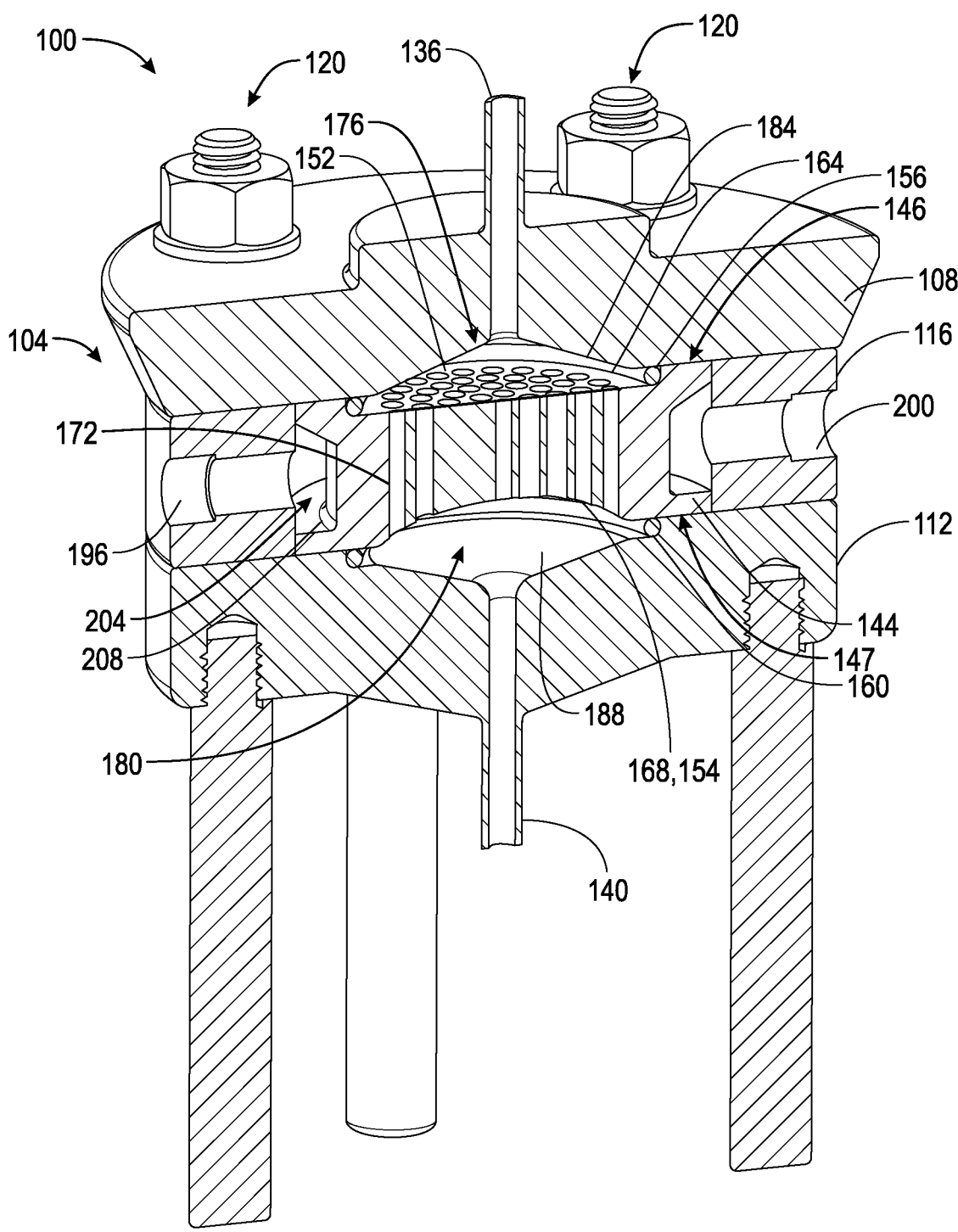
FIG. 5 is a cross-sectional view of the filter holder of FIG. 3.

With reference to FIGS. 4 and 5, the middle housing portion 116 surrounds and may at least partially support a filter support member 144. In the illustrated embodiment, the filter support member 144 is concentrically supported within the middle housing portion 116. That is, the middle housing portion 116 surrounds an outer periphery of the filter support member 144. In some embodiments, the filter support member 144 may be integrally formed with the middle housing portion 116. In other embodiments, the filter support member 144 may be formed separately and fixed to the middle housing portion 116 by welding, brazing, a threaded connection, or by any other suitable means.

The illustrated filter support member 144 includes an upstream side 146 facing the inlet 136 and a downstream side 147 opposite the upstream side 146 and facing the outlet 140. A first or upper recess 148 is formed in the upstream side 146 and is configured (i.e. sized and shaped) to receive a membrane filter assembly 152 (FIG. 4). The membrane filter assembly 152 has a circular perimeter in the illustrated embodiment; however, the shape of the membrane filter assembly 152 (and the corresponding shape of the upper recess 148) may vary in other embodiments. For example, in some embodiments, the membrane filter assembly 152 and the upper recess 148 may be oval shaped, square, hexagonal, etc.

The membrane filter assembly 152 may include one or more membrane filters with a diameter between 5 mm and 600 mm, and preferably between 13 mm and 293 mm. For example, the membrane filter assembly 152 may have a diameter of 13 mm, 25 mm, 47 mm, 90 mm, 142 mm, or 293 mm in certain embodiments. Each of the one or more membrane filters in the membrane filter assembly 152 may have a pore size between, for example, about 10 nanometers and about 1 micrometer. In some embodiments, each membrane filter may have a pore size between about 50 nanometers and about 200 nanometers. In some embodiments, each membrane filter may have a pore size of about 100 nanometers. Membrane filters according to such embodiments may be particularly suited for extruding liposomes. The membrane filters may be made of polycarbonate. In other embodiments, the membrane filter assembly 152 may include one or more membrane filters made of other materials (such as polyethylene terephthalate, aluminum oxide, or any other suitable membrane material), as well as other dimensions and/or pore sizes.

In some embodiments, the membrane filter assembly 152 may include a drain disk (e.g., a polyester drain disk) to provide support, improve flow, and prevent crinkling and tearing of the membrane filter(s) within the membrane filter assembly 152. In such embodiments, the membrane filter or filters are placed on top of the drain disk. It is also possible to insert drain disks between membrane filters. In some embodiments, membrane filter(s) and drain disk(s) may be placed on a filter support mesh or screen. Thus, the membrane filter assembly 152 includes at least one membrane filter and optionally includes one or more drain disks and/or a filter support screen. This assembly is placed into the first or upper recess 148 formed in the upstream side 146.

Referring to FIG. 5, the illustrated filter support member 144 further includes a lower recess 154 formed in the downstream side 147. An upper seal 156 surrounds the upper recess 148 at an interface between the filter support member 144 and the upper housing portion 108, and a lower seal 160 surrounds the lower recess 154 at an interface between the filter support member 144 and the lower housing portion 112. In the illustrated embodiment, the upper and lower seals 156, 160 are o-rings (e.g., made of rubber or any other suitable elastomeric or non-elastomeric sealing material), but other types of seals may be used. The seals 156, 160 may be compressed between the filter support member 144 and the upper and lower housing portions 108, 112, respectively, when the housing 104 is assembled.

Figure 6:
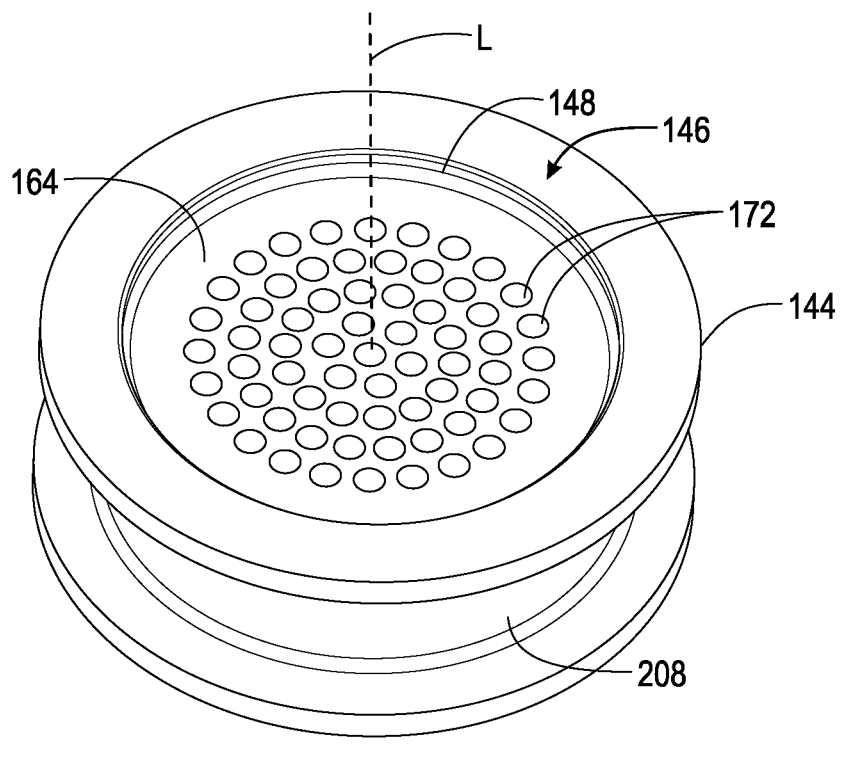
FIG. 6 is a top perspective view illustrating a filter support member of the filter holder of FIG. 3.
Figure 7:
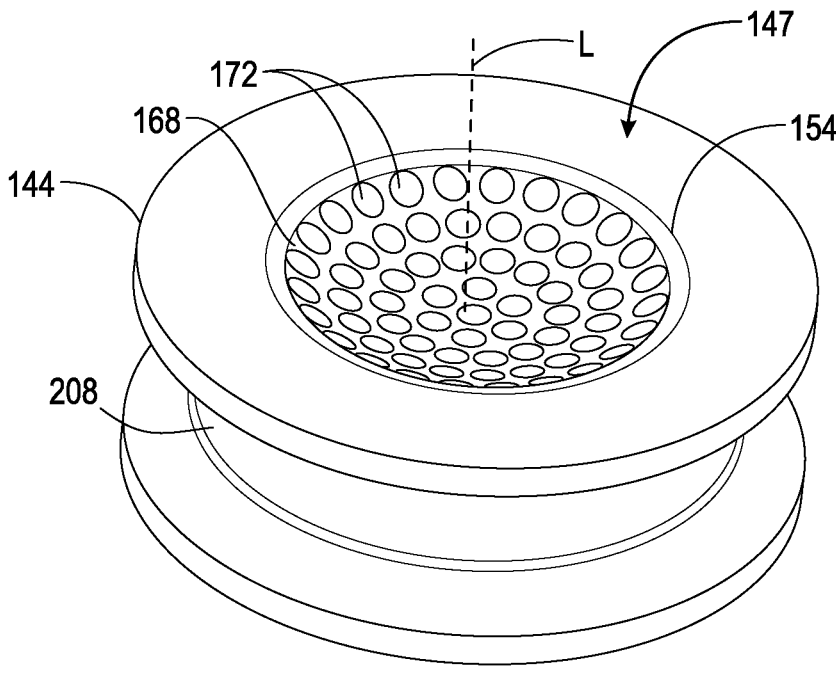
FIG. 7 is a bottom perspective view of the filter support member of FIG. 5.
Figure 8:
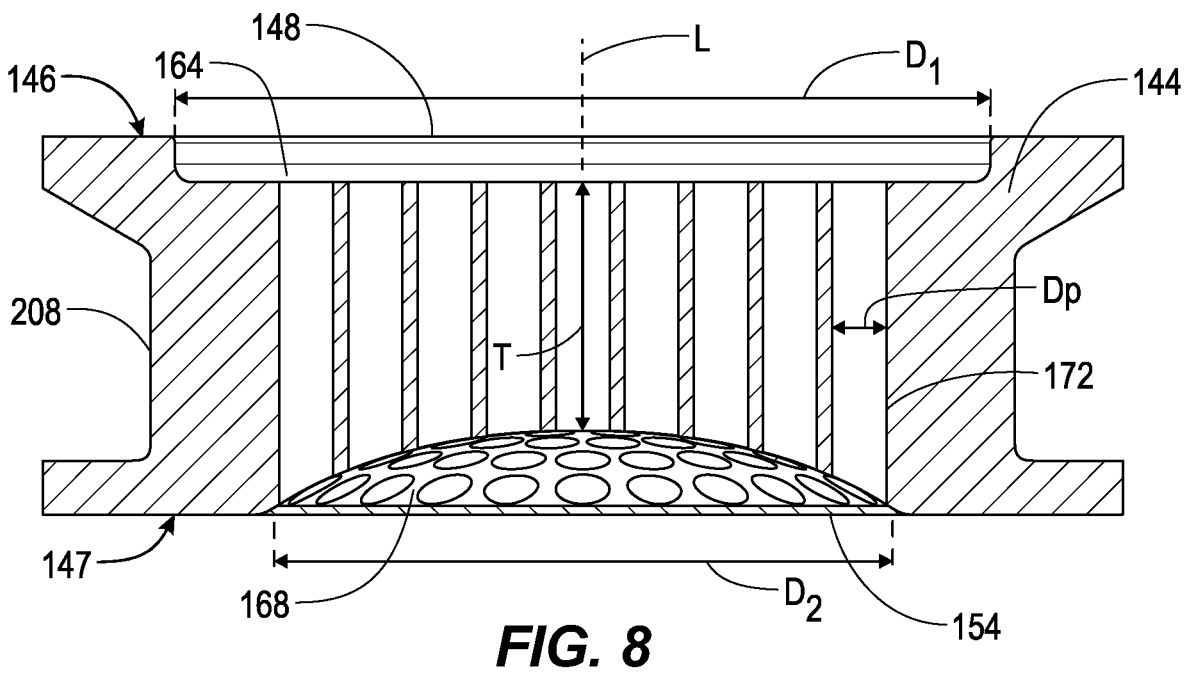
FIG. 8 is a cross-sectional view of the filter support member of FIG. 5.

With reference to FIGS. 6-8, the illustrated filter support member 144 includes a filter support surface 164 within the upper recess 148 and an outlet surface 168 within the lower recess 154. The outlet surface 168 is disposed opposite the filter support surface 164. In some embodiments, the lower recess 154 may be omitted, such that the outlet surface 168 may be generally flush with the remainder of the filter support member 144 and/or middle housing portion 116.

The filter support surface 164 has a diameter or maximum width D1 (FIG. 8) that is sized to receive the membrane filter assembly 152. For example, in some embodiments, the diameter D1 may be between about 5 mm and about 600 mm, and preferably between about 13 mm and about 293 mm, to accommodate membrane filter assemblies 152 having corresponding diameters. For example, the diameter D1 may be 13 mm, 25 mm, 47 mm, 90 mm, 142 mm, or 293 mm in certain embodiments. In the illustrated embodiment, the filter support surface 164 is planar; however, the filter support surface 164 may be non-planar (e.g., concave or convex) in other embodiments.

The outlet surface 168 defines a maximum width D2, which may be between about 0.5 inches (or 12.7 mm) and about 15 inches (or 381 mm) in some embodiments. In the illustrated embodiment, the outlet surface 168 is a curved, concave surface. The outlet surface 168 may be hemispherical, torispherical, ellipsoidal, or frustoconical, for example. In other embodiments, the outlet surface 168 may be flat.

A plurality of passages 172 extends between and through the surfaces 164, 168. In some embodiments, the filter support member 144 includes between 4 and 3,000 passages 172. In the embodiment illustrated in FIG. 8, the passages 172 extend parallel to the longitudinal axis L. In another embodiment, illustrated in FIG. 8A, one or more of the passages 172 may extend at a non-zero angle relative to the longitudinal axis L. For example, one or more of the passages 172 may extend at angles between about 5 degrees and about 60 degrees relative to the longitudinal axis L in some embodiments, or at an angle of about 10 degrees in some embodiments. In the embodiment illustrated in FIG. 8A, the maximum width D2 of the outlet surface 168 is less than the diameter D1 of the filter support surface 164. In other embodiments, the maximum width D2 of the outlet surface 168 may be equal to or greater than the diameter D1 of the filter support surface 164.

Figure 8A:
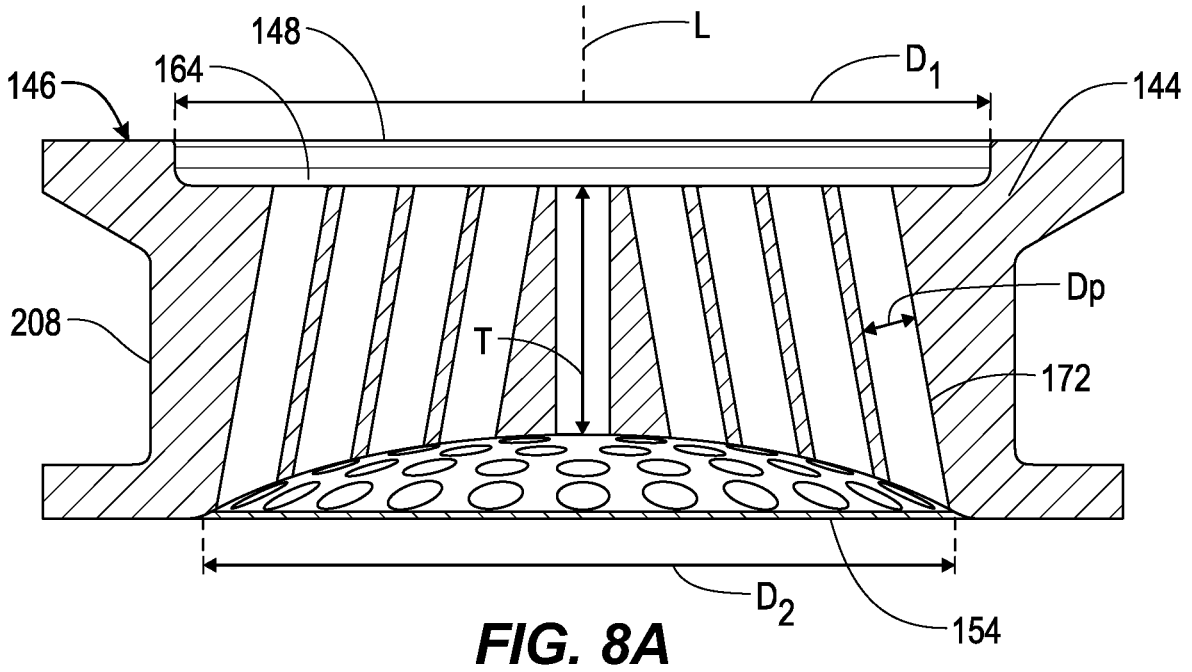
FIG. 8A is a cross-sectional view of a filter support member according to another embodiment.

Referring to FIGS. 8 and 8A, each of the passages 172 is cylindrical, with a constant diameter Dp between about 0.0625 inches (or 1.59 mm) and about 0.25 inches (or 6.35 mm). In other embodiments, the diameter Dp of each of the passages 172 may be about 0.125 inches (or 3.175 mm). Each of the passages 172 may have the same diameter Dp, or different passages 172 of the plurality of passages 172 may have different diameters Dp. In yet other embodiments, one or more of the passages 172 may have a variable diameter Dp, (e.g., such that the passage(s) 172 may have a conical shape).

The filter support member 144 has a minimum thickness T between about 0.125 inches (or 3.175 mm) and about 5 inches (or 127 mm) in some embodiments. The thickness T is sized to provide the filter support member 144 with sufficient strength to withstand pressure forces exerted on the filter support member 144 during extrusion. The curved design of the outlet surface 168 advantageously provides the filter support member 144 with high strength while minimizing the thickness T. This allows to reduce the weight and footprint and as a result increase the ease of handling of large commercial-scale extrusion equipment in particular for applications where high extrusion pressures in the range of several thousand psi are required.

Referring to FIG. 5, the inlet 136 is in fluid communication with an inlet cavity 176 adjacent the upstream side 146 of the filter support member 144, and the outlet 140 is in fluid communication with an outlet cavity or drain cavity 180 adjacent the downstream side 147 of the filter support member 144. In the illustrated embodiment, the inlet cavity 176 is at least partially defined by the filter support surface 164, the upper seal 156, and a recess 184 formed in the underside of the upper housing portion 108. The recess 184 has a generally frustoconical shape in the illustrated embodiment, tapering outward from the inlet 136. The frustoconical shape of the recess 184 may aid in distributing the material to be extruded over the surface of the membrane filter assembly 152. The outlet cavity 180 is at least partially defined by the outlet surface 168 of the filter support member 144, the lower seal 160, and a recess 188 formed on the top side of the lower housing portion 112. Like the recess 184, the recess 188 has a generally frustoconical shape, tapering outward from the outlet 140. The frustoconical shape of the recess 188 may facilitate flow of extrudate from the outlet cavity 180 to the outlet 140. In other embodiments, the recess 184 and/or the recess 188 may be cylindrical or have other shapes.

Figure 5A:
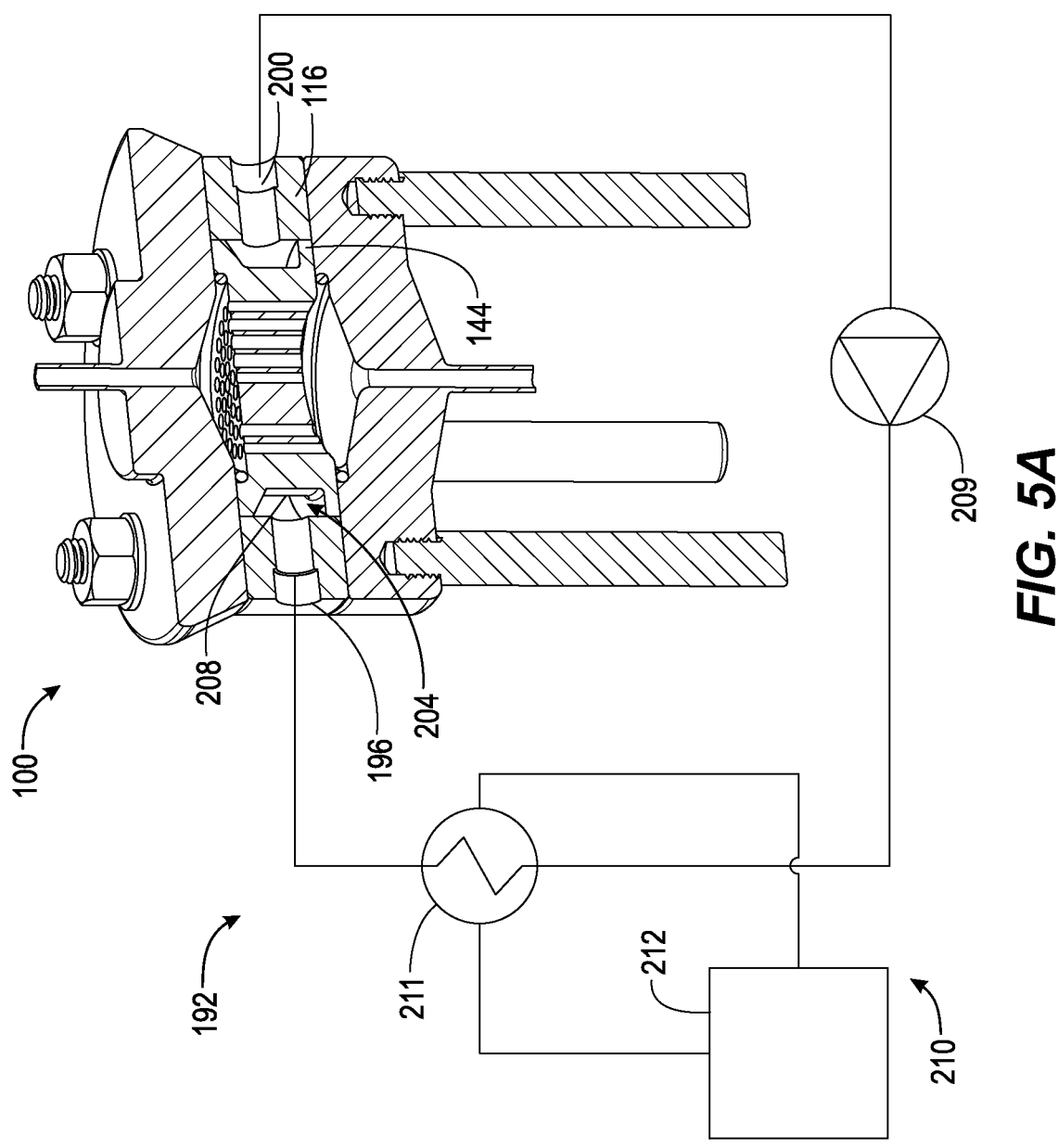
FIG. 5A is a schematic illustration of the filter holder of FIG. 3 coupled to a temperature regulating assembly.

With reference to FIG. 5A, the filter holder 100 may further include a temperature regulating assembly 192. In the illustrated embodiment, the middle housing portion 116 includes a fluid inlet port 196 and a fluid outlet port 200. The fluid inlet and outlet ports 200 are in fluid communication with a generally annular volume 204 surrounding the filter support member 144. In the illustrated embodiment, the filter support member 144 includes a circumferential groove 208, and the annular volume 204 is at least partially defined within the circumferential groove 208.

The temperature regulating assembly 192 may include a heating/cooling system such as a heating/cooling bath or a fully integrated heating/cooling process temperature control system (for example, a Mokon® system) coupled to the fluid inlet port 196 and/or the fluid outlet port 200 to circulate a heat-transfer fluid through the annular volume 204 and thereby efficiently heat or cool the filter support member 144. For example, in some embodiments, the temperature regulating assembly 192 includes a fluid circulator such as a pump 209 and a heat transfer system 210 including a heat exchanger or heating cooling aggregate 211 and a temperature control device 212. The heat-transfer fluid may include air, water, glycol, refrigerants, or the like. In some embodiments, the filter support member 144 may include dimples or other flow-affecting features in the circumferential groove 208 to create turbulence within the flow of heat-transfer fluid, thereby enhancing heat transfer by convection.

In some embodiments, the heat-transfer system 210 may be omitted, and the filter support member 144 may be heated or cooled by the heat-transfer fluid via natural convection. In some embodiments heating/cooling could also be achieved through a heating coil or band or heat blanket around the outside perimeter of the filter holder or immersion of the filter holder into a heating/cooling liquid/bath.

The temperature regulating assembly 192 may be configured differently in other embodiments. For example, in some embodiments, the temperature regulating assembly 192 may include a coil wrapped around and in thermally-conductive contact with the filter support member 144. Heat transfer fluid may be conveyed through the coil to heat or cool the filter support member 144. In yet other embodiments, the filter holder 100 may not include a temperature regulating assembly 192.

Referring to FIG. 5, in operation, a material to be extruded enters through the inlet 136 of the filter holder 100 at an elevated extrusion pressure (e.g., between about 50 psi and about 2,500 psi in some embodiments, or greater than 2,500 psi in some embodiments). The material to be extruded flows through the inlet 136 and into the inlet cavity 176, where it disperses over the membrane filter assembly 152 (FIG. 5). The material is forced through pores in the membrane filter under pressure, and the extrudate flows through the channels 172 and into the outlet cavity 180. From the outlet cavity 180, the extrudate flows out of the filter holder 100 through the outlet 140. The temperature regulating assembly 192 (FIG. 5A) may regulate the temperature of the filter support member 144 by controlling the temperature and/or flow rate of the temperature control fluid.

Figure 1:
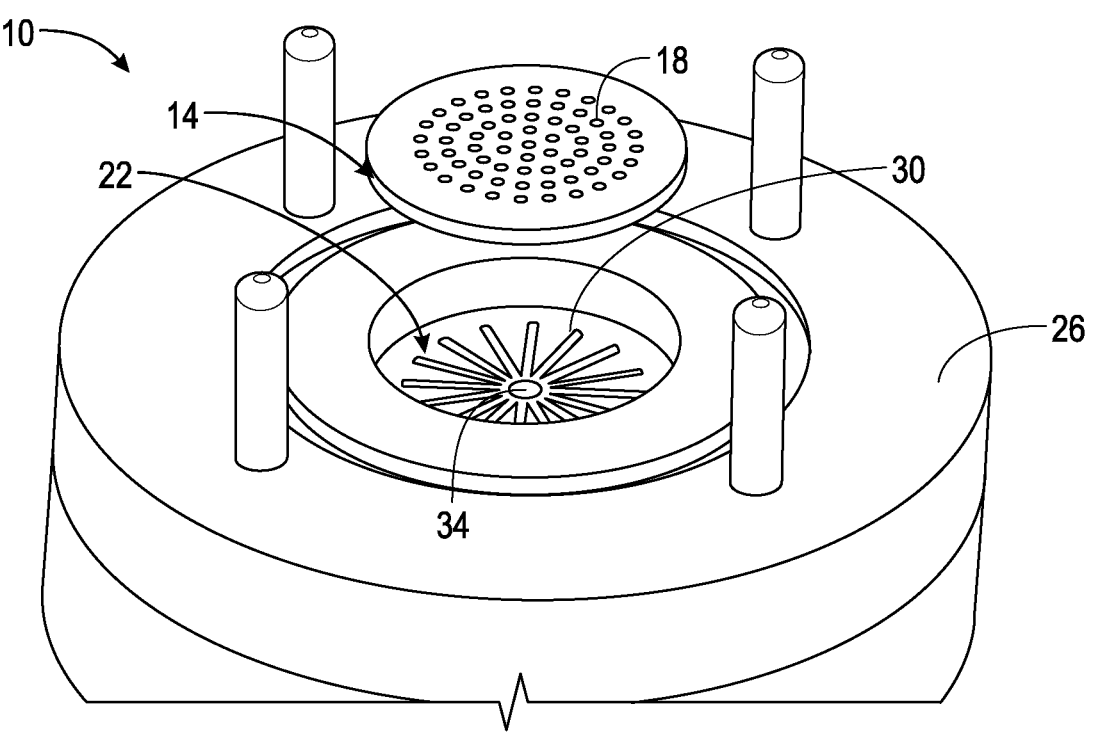
FIG. 1 is an exploded view of a prior art filter holder.
Figure 2:
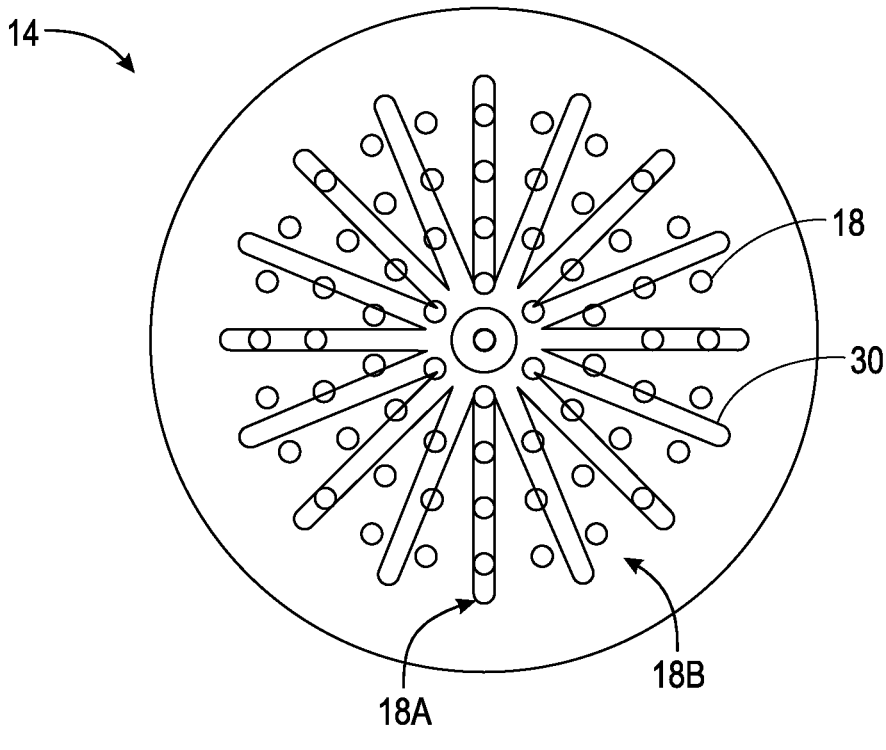
FIG. 2 is a top view illustrating passages and channels of the filter holder of FIG. 1.

The filter holder 100 described and illustrated herein advantageously provides a high utilization of the membrane filter(s), which in turn reduces clogging and fouling of the membrane filter(s) as well as extrusion pressure. In particular, the inlet and outlet cavities 176, 180 provide increased filter utilization and reduced extrusion pressure. Rather than communicating with discrete channels 30 like in existing filter support assemblies, the passages 172 of the filter holder 100 open directly to the cavities 176, 180. As such, none of the passages 172 are blocked. Additionally, the passages 172 may be more numerous and/or larger in diameter than the passages 18 in existing filter support assemblies (FIGS. 1-2).

This configuration of the passages 172 reduces flow resistance and further increases the area on the membrane filter(s) of the membrane filter assembly 152 through which the material can flow.

The filter support member 144 may be thicker than the filter support disc 14 in existing filter support assemblies to provide the requisite strength to withstand high pressures experienced during extrusion. However, the concave outlet surface 168 of the filter support member 144 allows the thickness and mass of the filter support member 144 to be minimized and also provides volume for the outlet cavity 180. In some embodiments, the filter holder 100 be rated at pressures up to 2,500 psi. In some embodiments, the filter holder 100 may be rated at pressures greater than 2,500 psi.

Computational fluid dynamics simulation testing of the filter holder 100 demonstrated significant increases in filter utilization and decreases in extrusion pressure compared to the filter holder 10 for a constant flow rate. The results of the testing are listed in Table 1:

TABLE 1

|  | Filter holder 10 | Filter holder 100 |
|---|---|---|
| Flow Rate (mL/min) | 100 | 100 |
| Pressure (psig) | 410 | 117 |
| Area of Filter Being Used | 5% | 30% |

Thus, the filter holder 100 provided a 500% increase in effective filter area and a 71% decrease in extrusion pressure compared to the filter holder 10.

By increasing the effective filter area, the membrane filter(s) of the membrane filter assembly 152 may be used for a longer period of time without clogging or fouling. This may reduce processing time and cost, and improve the quality of the extrudate. Furthermore, due to the lower extrusion pressure and the higher maximum operating pressure provided by the filter holder 100, a greater number of membrane filters can be stacked on top of one another. This may increase the size reduction potential of the extruder and allow certain products to be extruded in a single pass that would otherwise require multiple passes through the extruder.

Figure 9:
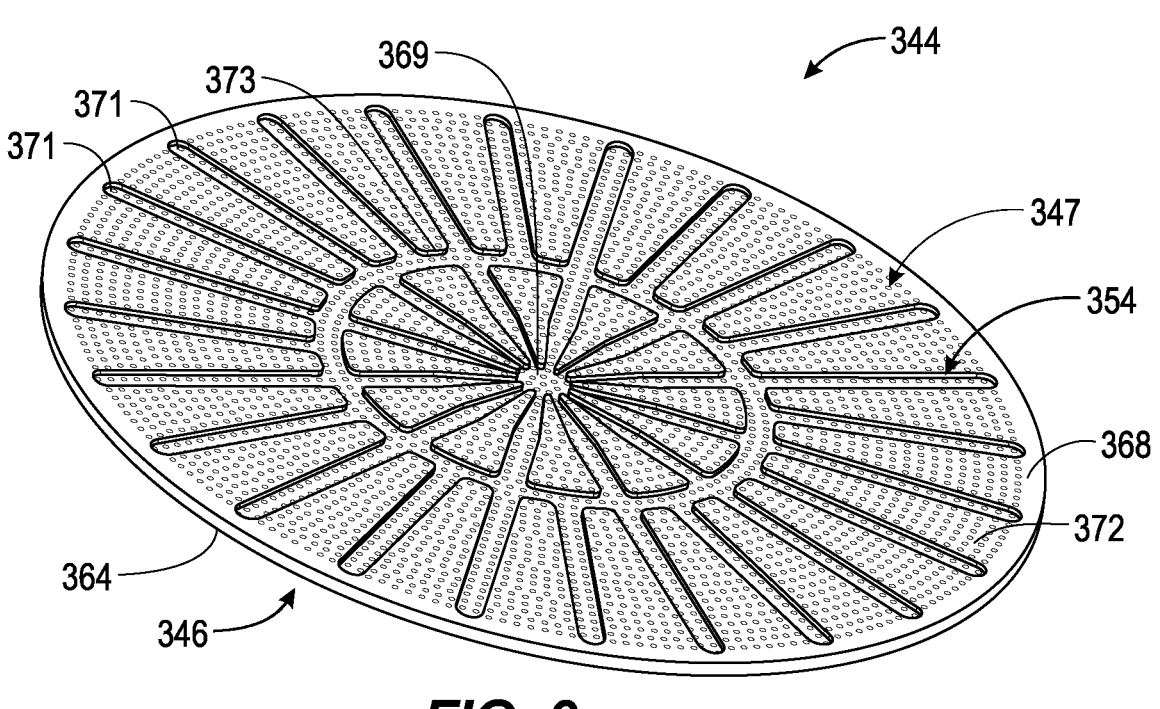
FIG. 9 is a perspective view of a filter support member according to another embodiment.

FIG. 9 illustrates a filter support member 344 according to another embodiment. The filter support member 344 is configured as a filter support disc that may replace the flat filter support discs of existing filter holders, such as the filter support disc 14 of the filter holder 10 described above with reference to FIG. 1.

The illustrated filter support member 344 includes an upstream side 346, a downstream side 347 opposite the upstream side 346, and a plurality of passages 372 extending between the upstream side 346 and the downstream side 347. The upstream side 346 includes a planar filter support surface 364 configured to support a membrane filter. The downstream side 347 includes an outlet surface 368 opposite the filter support surface 364, a central relief 369, a plurality of radial channels 371 extending radially outward from the central relief 369, and an annular channel 373 disposed radially between the central relief 369 and an outer periphery of the filter support member 344.

The central relief 369, radial channels 371, and annular channel 373 are interconnected and collectively define a lower recess 354 formed in the downstream side 347 of the filter support member 344. In other embodiments, the lower recess 354 may be defined by other combinations and/or arrangements of channels formed in the downstream side 347 of the filter support member 344. The lower recess 354 at least partially defines an outlet cavity that allows for flow through a greater number of passages 372 than existing filter support discs 14, thereby increasing the effective area of the membrane filter, reducing clogging and fouling, and reducing extrusion pressure. In some embodiments, the central relief 369, radial channels 371, and annular channel 373 may at least partially align with the channels 30 in the housing plate 26 (FIG. 1). In such embodiments, the outlet cavity may be collectively defined by the lower recess 354 and the channels 30.

Figure 10:
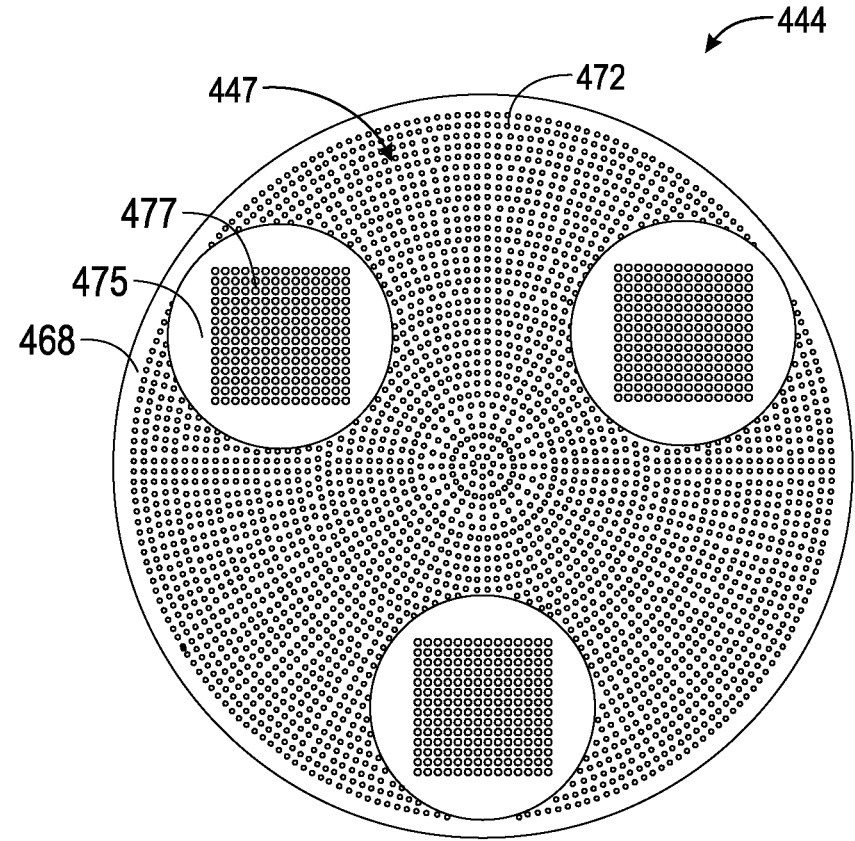
FIG. 10 is a bottom view of a filter support member according to another embodiment.

FIG. 10 illustrates a filter support member 444 according to another embodiment. Like the filter support member 344 described above with reference to FIG. 9, the filter support member 444 is configured as a filter support disc that may replace the flat filter support discs of existing filter holders, such as the filter support disc 14 of the filter holder 10 (FIG. 1).

The illustrated filter support member 444 includes an upstream side (not shown), a downstream side 447 opposite the upstream side, and a plurality of passages 472 extending between the upstream side and the downstream side 447. The upstream side includes a planar filter support surface configured to support a membrane filter. The downstream side 447 includes an outlet surface 468 opposite the filter support surface. A plurality of spacers 475 is positioned against the downstream side 447. In the illustrated embodiment, three spacers 475 are provided; however, any other number of spacers 475 may be used.

The spacers 475 may have a thickness between about 0.01 inches and about 0.5 inches in some embodiments, between about 0.02 inches and about 0.3 inches in some embodiments, between about 0.05 and about 0.15 inches in some embodiments, or about 0.1 inches in some embodiments. The spacers 475 are preferably sized such that the filter support member 444 may still be accommodated within the recess 22 of existing filter supports 10 (FIG. 1). In the illustrated embodiment, the spacers 475 include passages 477 that may align and/or fluidly communicate with overlapping passages 472 in the filter support member 444; however, the passages 477 may be omitted in other embodiments.

When the filter support member 444 is positioned within the recess 22 of the housing plate 26 (FIG. 1), the spacers 475 maintain a gap between the downstream side 447 of the filter support member 444 and the opposing surface of the recess 22. This gap provides an outlet cavity adjacent the downstream side 447 of the filter support member 444 thereby increasing the effective area of the membrane filter, reducing clogging and fouling, and reducing extrusion pressure.

Because the filter support members 344, 444 described above with reference to FIGS. 9 and 10 maintain the disc configuration of existing filter support discs 14 (FIG. 1), the filter support member 444 may be advantageously incorporated into existing filter holders, such as the filter holder 10, in order to provide improved performance.

Testing of the filter support members 344, 444 demonstrated pressure reduction due to improved filter utilization compared to an existing filter support disc 14. Water was pumped at a constant flow rate of 3 liters per minute through a series of three membrane filters, each having a pore size of 100 nanometers. The tested filter support disc 14 and filter support members 344, 444 each had a nominal diameter of 293 millimeters. The results of this testing are summarized in Table 2:

TABLE 2

| | Filter Support Disc 14 | Filter Support Member 344 | Filter Support Member 444 |
|---|---|---|---|
| Flow Rate (L/min) | 3 | 3 | 3 |
| Pressure (psig) | 430 | 330 | 190 |
| Pressure Reduction | — | 23% | 56% |

Thus, the filter support member 344 of FIG. 9 advantageously provided a 23% reduction in extrusion pressure compared to the filter support disc 14 of FIG. 1, and the filter support member advantageously provided a 56% reduction in extrusion pressure compared to the filter support disc 14 of FIG. 1.

Figure 11:
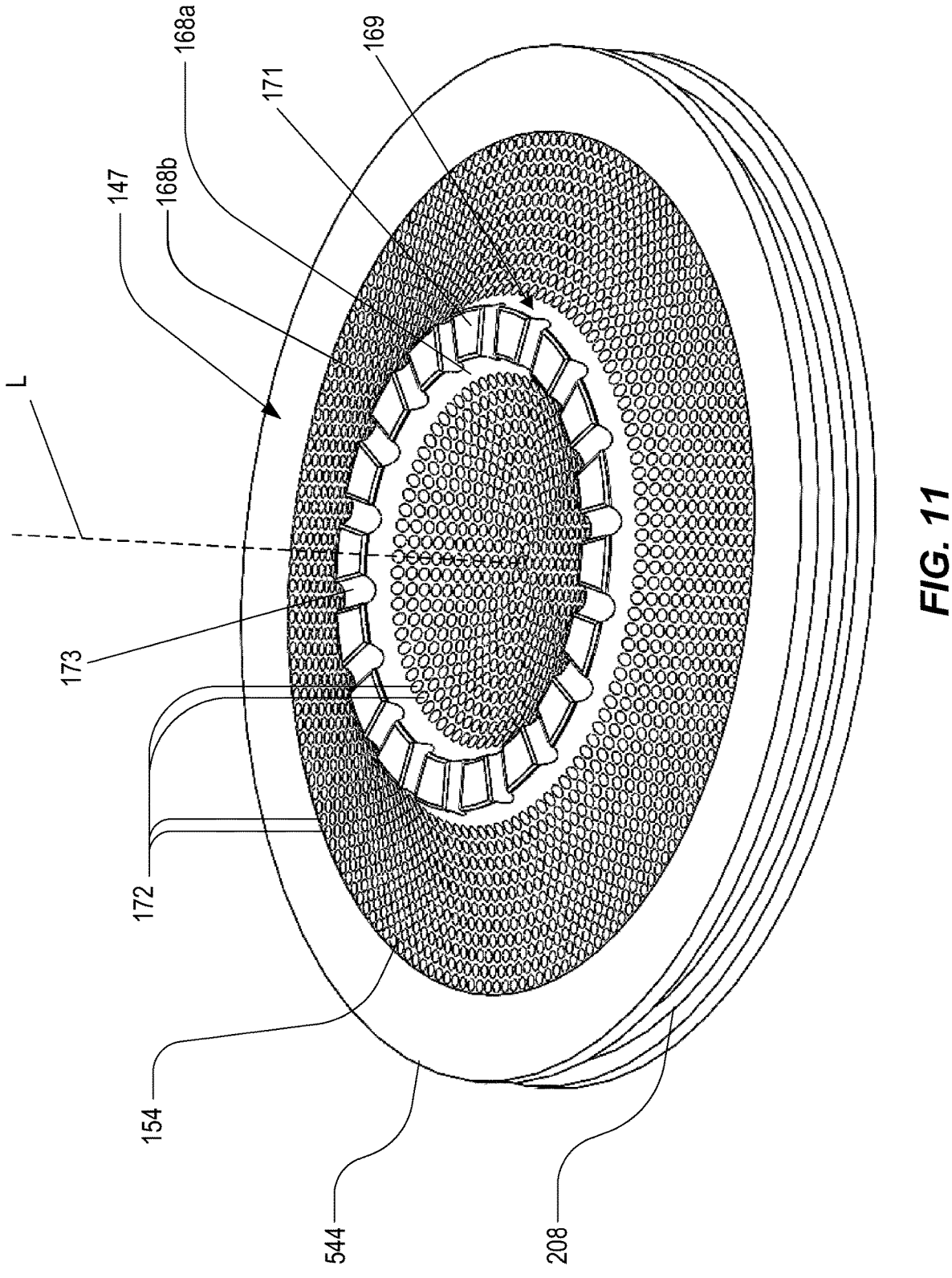
FIG. 11 is a bottom perspective view illustrating a filter support member according to another embodiment.
Figure 12:
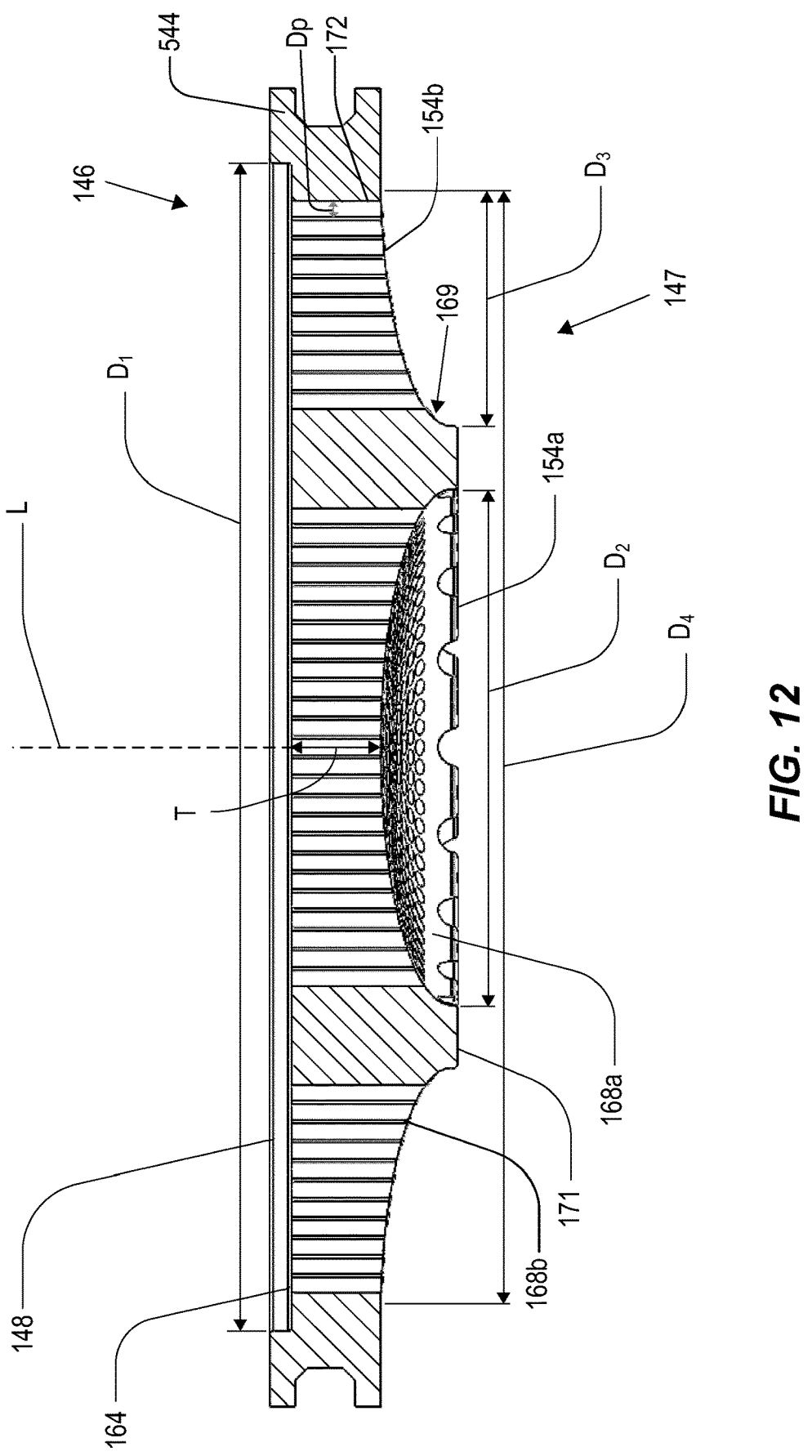
FIG. 12 is a cross-sectional view of the filter support member of FIG. 11.

FIGS. 11 and 12 illustrate a filter support member 544 according to another embodiment. The filter support member 544 is similar to the filter support member 144, and features of the filter support member 544 corresponding with features of the filter support member 144 described above are given identical reference numbers.

Referring to FIG. 12, the illustrated filter support member 544 includes an upstream side 146 having an upper recess 148 and filter support surface 164 within the upper recess 148. A downstream side 147 of the filter support member 544 includes a first lower recess 154a and a second lower recess 154b. The first lower recess 154a is centered along the axis L, and the second lower recess 154b surrounds the first lower recess 154a. An annular support wall 169 extends between the first lower recess 154a and the second lower recess 154b. The first lower recess 154a includes a first outlet surface 168a, and the second lower recess 154b includes a second outlet surface 168b.

In the illustrated embodiment, the filter support surface 164 has a diameter or maximum width D1 that is sized to receive the membrane filter assembly 152. In the illustrated embodiment, the diameter D1 is 293 mm, although the diameter of D1 may vary in other embodiments. The first outlet surface 168a defines a maximum width D2, and the second outlet surface 168b defines a width D3. The outer diameter of the second outlet surface 168b defines a diameter D4. In the illustrated embodiment, D2 is about 5.1 inches (or 129.4 mm), D3 is about 2.25 inches (or 57.2 mm), and D4 is about 10.84 inches (or 275.4 mm). Thus, a ratio of D2:D4 is about 1:2 in the illustrated embodiment. In other embodiments, the ratio of D2:D4 may be between 1:1 and 1:5.

A plurality of passages 172 extends between and through filter support surface 164 and the first and second outlet surfaces 168a, 168b. In the embodiment illustrated in FIGS. 8B-8C, the passages 172 extend parallel to the longitudinal axis L; however, one or more of the passages 172 may extend at a non-zero angle relative to the longitudinal axis L. In the illustrated embodiment, the passages 172 do not extend through the annular support wall 169.

Referring to FIG. 11, the annular support wall 169 includes a plurality of planar support surfaces 171 separated in an alternating manner by a plurality of radial channels 173. When the filter support member 544 is assembled with a filter holder, such as the filter holder 100, the support surfaces 171 engage an upper side of the lower housing portion 112. In some embodiments, the support wall 169 may be positioned at a mid-point of the radius of the filter support member 544. The additional support provided by the support wall 169 allows the filter support member 544 to be used at high extrusion pressures without deforming. The radial channels 173 provide fluid flow paths from the second lower recess 154b to the first lower recess 154a.

Figure 13:
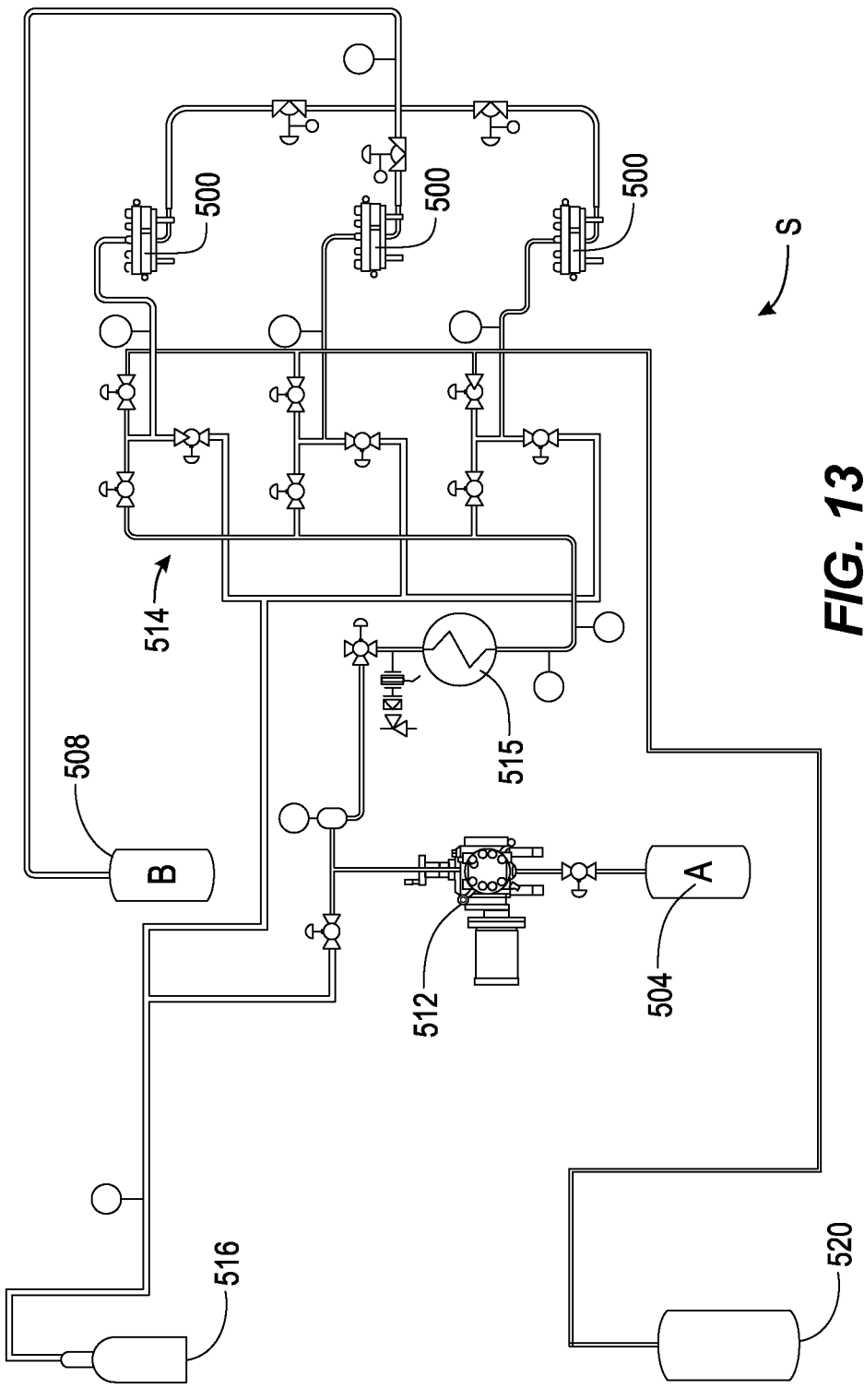
FIG. 13 is a schematic illustration of an extrusion system according to an embodiment of the present disclosure.

FIG. 13 illustrates an extrusion system S according to an embodiment of the present disclosure. The illustrated extrusion system S includes a plurality of filter holders 500, such as the filter holder 100 described above with reference to FIGS. 3-8, and/or a filter holder incorporating one of the filter support members 344, 444, 544 described above with reference to FIGS. 9-12, arranged fluidly between a supply reservoir 504 containing a material to be extruded and a collection reservoir 508 configured to receive extrudate from the filter holders 500. The illustrated system S also includes a pressure source 512, such as a pump, operable to draw the material to be extruded from the supply reservoir 504 and to pressurize the material to be extruded for distribution to the filter holders 500.

The supply reservoir 504, collection reservoir 508, pressure source 512, and filter holders 500 are interconnected by a fluid transfer assembly 514, which includes fluid transfer components such as piping, valving, pressure relief, sensing, and/or metering components. In addition, the extrusion system S may include one or more heat exchangers 515 for regulating a temperature of the material before and/or after extrusion. In the illustrated embodiment, the filter holders 500 are connected in parallel between the supply reservoir 504 and the collection reservoir 508. As such, each filter holder 500 may be operated individually or simultaneously during an extrusion operation. This may provide the system S with greater throughput capacity compared to a system with a single filter holder 500. In other embodiments, one or more filter holders 500 may be connected in series. In such embodiments, a greater size reduction may be achieved in the extrudate in a single pass.

With continued reference to FIG. 13, the illustrated system S further includes a purging gas supply 516 and a pressure relief capture vessel 520. The purging gas supply 516 may contain a pressurized gas, such as air, nitrogen, carbon dioxide, argon, or any other gas suitable for clearing material from the fluid transfer assembly 514 (e.g., for cleaning purposes, maintenance, etc.). The pressure relief capture vessel 520 may be configured to receive vented gas or liquid discharged from one or more pressure relief valves of the fluid transfer assembly 514.

The following examples illustrate the improved performance of a liposome extruder equipped with the prior art filter holder of FIG. 1, ("LIPEX 1"), versus a liposome extruder equipped with a filter holder embodying aspects of the present disclosure, such as the filter holder of FIG. 3, ("LIPEX 2"). The examples were performed using the same control variables on both LIPEX 2 and LIPEX 1 of comparable size.

These examples demonstrate that LIPEX 2 can extrude a given liposome formulation at a significantly lower pressure, higher flow rate, and a larger total throughput than LIPEX 1. The following procedure was repeated for each size (25 mm and 47 mm) of extruders. The only controlled parameters that changed between each size was the reported Multilamellar Vesicle (MLV) volume and reported flow rate. At each size, the lowest reported flow rate represents the flow rate that would commonly be used by personnel experienced in the field. The higher reported flow rates represent flow rates that are commonly too high for most applications using LIPEX 1 and would result in too high of extrusion pressures in prior art, resulting in batch failure.

The lipid formulations described in the following Examples contained a 55:45 mol % ratio of egg phosphatidylcholine (EPC) and cholesterol, dissolved in anhydrous ethanol and hydrated with an aqueous ammonium sulfate buffer solution to a final concentration of 40 mg/mL. The chosen formulation was selected by way of example only and should not be regarded as limiting.

A lipid solution (400 mg/mL of EPC and cholesterol in anhydrous ethanol) was prepared, stirred, and heated at 50° C. A separate aqueous buffer solution (250 mM ammonium sulphate) was prepared, filtered through a 0.2/0.45 um Sartobran Size 4 filter, and added to the lipid solution to give a final lipid MLV concentration of 40 mg/mL. The MLV solution was mixed and heated at 50° C. for 5 minutes.

The following items were installed onto the filter support of the extruder, in order from bottom to top: 1×stainless steel support disc (LIPEX 1 only), 1×stainless steel support screen, 1×polyester drain disc, and 1×0.1 um track-etched polycarbonate membrane. The extruder was connected to a piston-pump via stainless steel tubing and fittings. A pressure gauge was installed inline to observe pressure measurements.

An initial aliquot of the MLV solution was taken and the particle size was measured. The MLV stock solution was then pumped at the reported flow rate through the extruder and into a receiving container, for a single extrusion pass. Additional extrusion passes were performed at the reported flow rate until either a maximum of 5 total extrusion passes were completed or until the extrusion pressure exceeded the maximum allowable working pressure of the extruder. If the pressure exceeded the maximum allowable working pressure of the extruder, the batch would be considered a failure. An aliquot was taken after each pass and measured for particle size. Pressure measurements were observed and recorded at the reported time increments.

Figure 14:
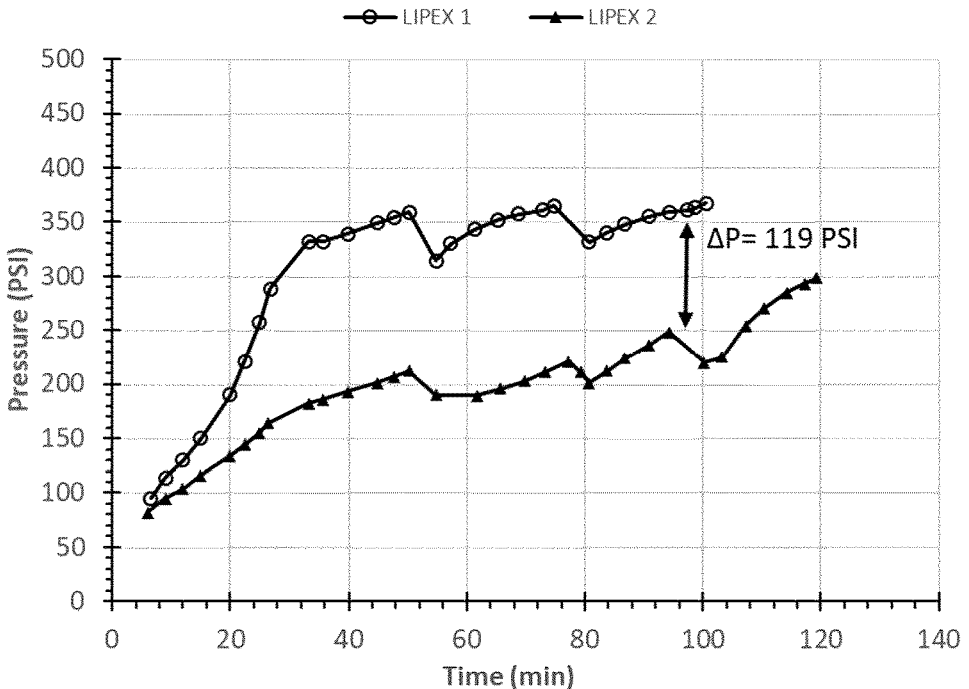
FIG. 14 is a graph comparing extrusion pressure of a liposome extruder equipped with the prior art filter holder of FIG. 1, ("LIPEX 1"), versus a liposome extruder equipped with a filter holder embodying aspects of the present disclosure, such as the filter holder of FIG. 3, ("LIPEX 2"), using a 47 mm filter at a flow rate of 10 mL/min.

FIG. 14 depicts a comparison of the extrusion pressure between 47 mm LIPEX 1 and LIPEX 2 extruders at a flow rate of 10 mL/min. The extrusion pressure of LIPEX 2 was on average, 119 PSI less than LIPEX 1, which is a 39% decrease in extrusion pressure.

Figure 15:
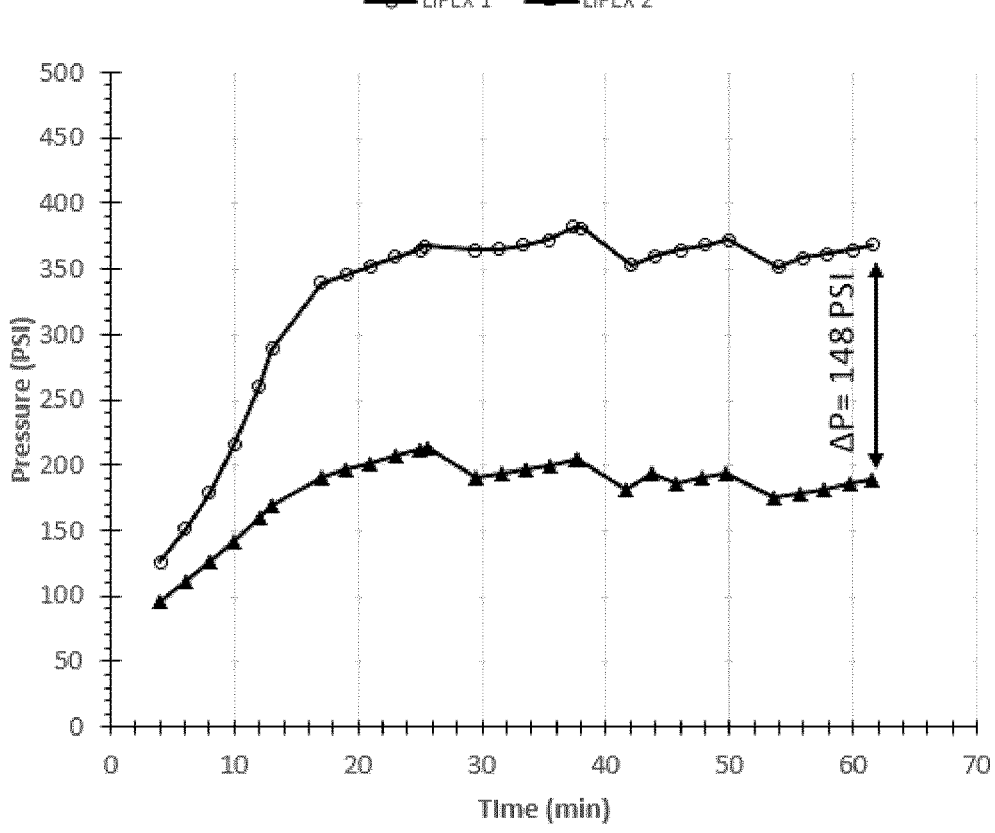
FIG. 15 is a graph comparing extrusion pressure of LIPEX 1 versus LIPEX 2 using a 47 mm filter at a flow rate of 20 mL/min.

FIG. 15 depicts a comparison of the extrusion pressure between 47 mm LIPEX 1 and LIPEX 2 extruders at a flow rate of 20 mL/min. The extrusion pressure of LIPEX 2 was on average, 148 PSI less than LIPEX 1, which is a 44% decrease in extrusion pressure.

Figure 16:
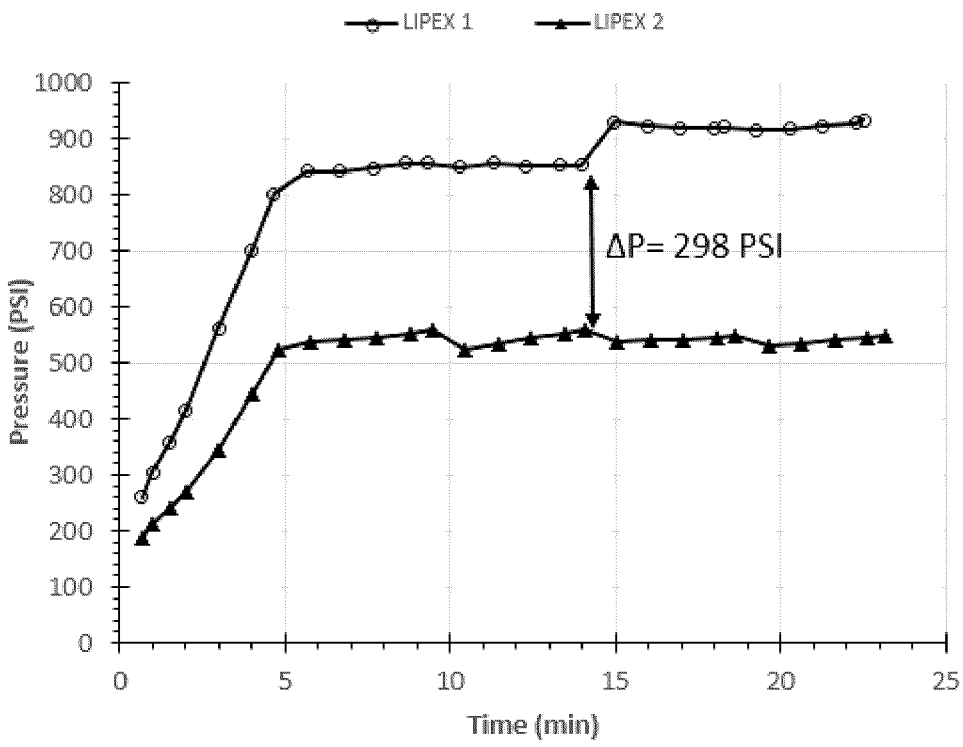
FIG. 16 is a graph comparing extrusion pressure of LIPEX 1 versus LIPEX 2 using a 47 mm filter at a flow rate of 110 mL/min.

FIG. 16 depicts a comparison of the extrusion pressure between 47 mm LIPEX 1 and LIPEX 2 extruders at a flow rate of 110 mL/min. The extrusion pressure of LIPEX 2 was on average, 298 PSI less than LIPEX 1, which is a 37% decrease in extrusion pressure.

Figure 17:
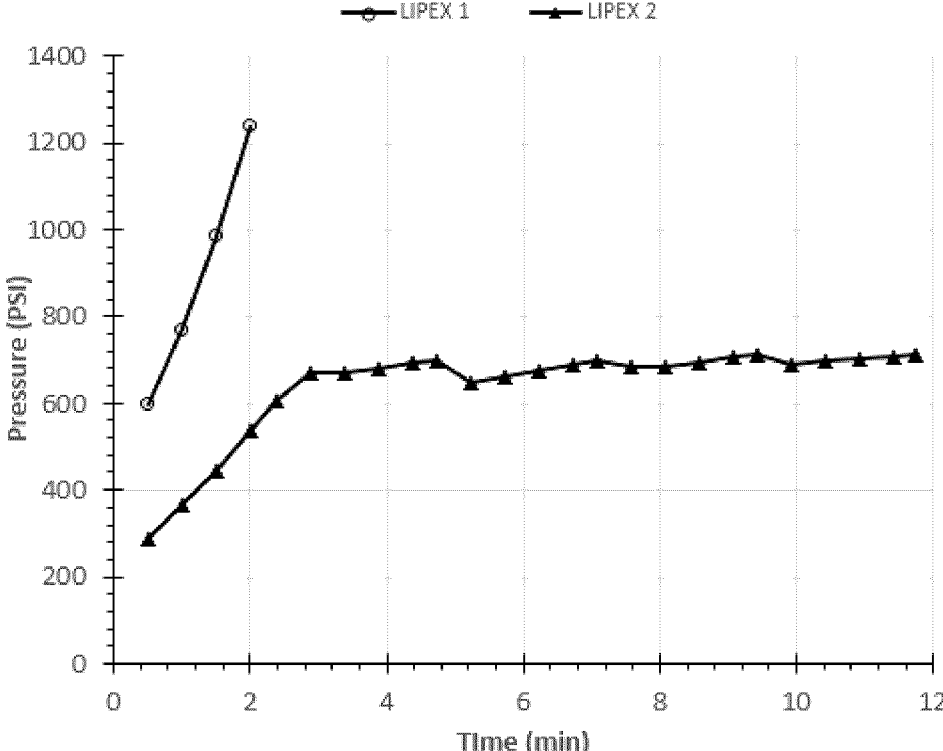
FIG. 17 is a graph comparing extrusion pressure of LIPEX 1 versus LIPEX 2 using a 47 mm filter at a flow rate of 220 mL/min.

FIG. 17 depicts a comparison of the extrusion pressure between 47 mm LIPEX 1 and LIPEX 2 extruders at a flow rate of 220 mL/min. LIPEX 1 resulted in a batch failure as it was only able to extrude for 2 minutes before the pressure exceeded the maximum working pressure. LIPEX 2, however, was able to extrude all 5 passes. The extrusion pressure of LIPEX 2 was on average, 627 PSI, which is an optimal extrusion pressure and is well below the maximum working pressure.

Figure 18:
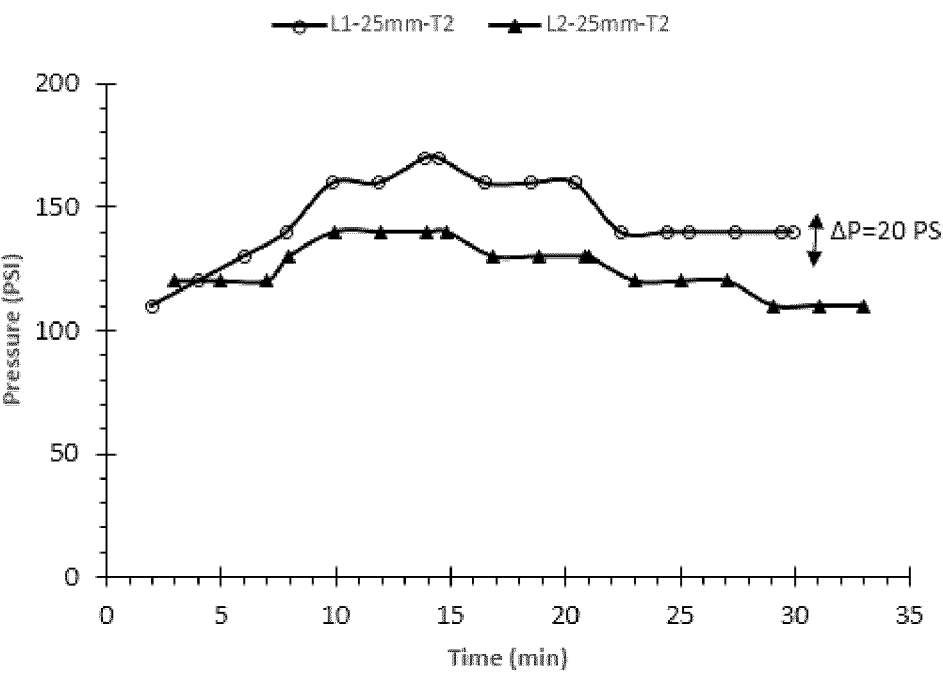
FIG. 18 is a graph comparing extrusion pressure of LIPEX 1 versus LIPEX 2 using a 25 mm filter at a flow rate of 5 mL/min.

FIG. 18 depicts a comparison of the extrusion pressure between 25 mm LIPEX 1 and LIPEX 2 extruders at a flow rate of 5 mL/min. The extrusion pressure of LIPEX 2 was on average, 15 PSI less than LIPEX 1, which is a 11% decrease in extrusion pressure.

Figure 19:
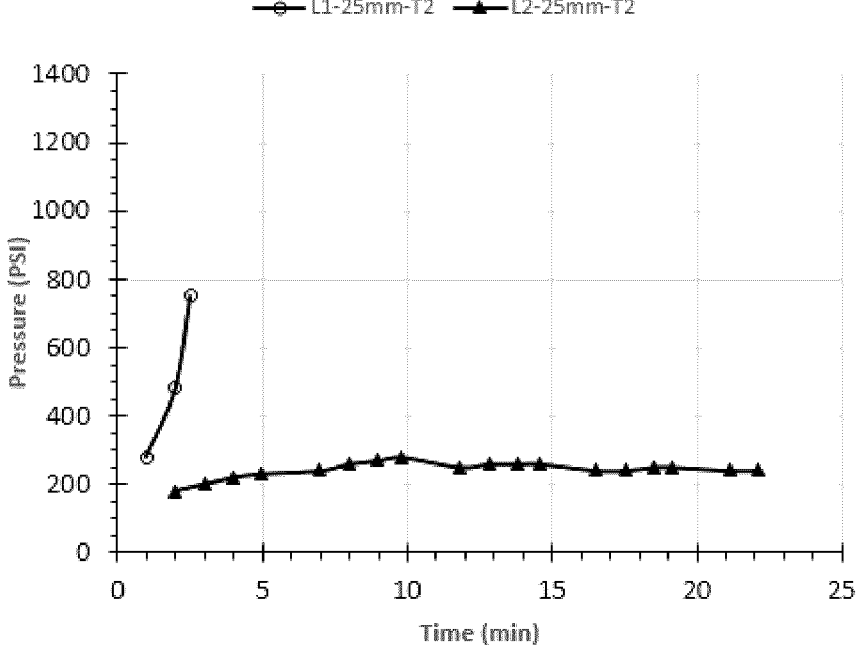
FIG. 19 is a graph comparing extrusion pressure of LIPEX 1 versus LIPEX 2 using a 25 mm filter at a flow rate of 25 mL/min.

FIG. 19 depicts a comparison of the extrusion pressure between 25 mm LIPEX 1 and LIPEX 2 extruders at a flow rate of 25 mL/min. LIPEX 1 resulted in a batch failure as it was not able to extrude more than 1 pass without the pressure exceeding the maximum working pressure of the extruder. LIPEX 2, however, was able to extrude all 5 passes. The extrusion pressure of LIPEX 2 was on average, 250 PSI, which is an optimal extrusion pressure and is well below the maximum working pressure.

To summarize, all of the above Examples showed significant decrease in extrusion pressure, which was even more evident as the flow rate and throughput was increased. For both the 25 mm and 47 mm extruder sizes at high flow rates, LIPEX 2 was able to successfully extrude the material through all 5 passes while LIPEX 1 consistently failed after 1-2 passes.

In another example, a flow simulation was conducted to provide a direct comparison of fluid dynamics between LIPEX 1 and LIPEX 2. SOLIDWORKS® 3D, a mechanical computer-aided design (CAD) and computational flow dynamics (CFD) simulation software, was used to simulate the fluid dynamics inside the extruders. These examples simulated water being pumped at a controlled flow rate through a comparable experimental setup as set forth in the examples above: an extruder with 1×stainless steel support disc (LIPEX 1 only), 1×stainless steel support screen, 1×polyester drain disc, and 1×0.1 um track-etched polycarbonate membrane installed. The resulting pressure drop across the filter membrane was observed and reported.

The simulation for each extruder was setup using the same method. Water was chosen as the simulation liquid. The reported volumetric flow rate at the inlet of the extruder, and a static pressure at the outlet of the extruder, were applied as the boundary conditions. A 0.1 um filter membrane, like the ones used in the examples above, was simulated using the SOLIDWORKS® Porous Membrane feature, along with the pressure vs. flow rate data from the examples above. Identical filter membrane characteristics were used for LIPEX 1 and LIPEX 2 so that a direct comparison could be made. The simulation was executed at each extruder size (25 mm, 47 mm, 90 mm, 142 mm, and 293 mm).

The filter membrane characteristics were extrapolated for the 90 mm, 142 mm, and 293 mm extruders. Since LIPEX 1 and LIPEX 2 used identical filter membrane characteristics, the resulting pressure could be evaluated and compared between LIPEX 1 and LIPEX 2 with confidence.

Table 3 below includes summarized data for each flow simulation:

TABLE 3

| Extruder Size | Flow Rate (mL/min) | LIPEX 1 Pressure (PSIG) | LIPEX 2 Pressure (PSIG) | % Decrease in Pressure with LIPEX 2 |
|---|---|---|---|---|
| 25 | 25 | 650 | 280.5 | 57% |
| 47 | 221 | 2009 | 604 | 70% |
| 90 | 451 | 656 | 326 | 50% |
| 142 | 1000 | 447 | 255 | 43% |

All of the simulations showed that LIPEX 2 can extrude at significantly less extrusion pressure at a given flow rate, compared to LIPEX 1. Inversely, this means that LIPEX 2 can extrude at a much higher flow rate than LIPEX 1, while maintaining a comparable extrusion pressure. Furthermore, the simulation results support the experimental results in the examples of FIGS. 14-19 discussed above.

Although the invention has been described in detail with reference to certain preferred embodiments, variations and modifications exist within the scope and spirit of one or more independent aspects of the invention as described.

Various features of the invention are set forth in the following claims.

Item 1 a filter holder for liposome extrusion, the filter holder comprising:

a housing including an inlet configured to receive a material to be extruded and an outlet;

a filter support member disposed within the housing between the inlet and the outlet, the filter support member including:

an upstream side having a filter support surface configured to support a membrane filter assembly, a downstream side opposite the upstream side, and a plurality of passages extending through the filter support member from the filter support surface to the downstream side; and an outlet cavity in fluid communication with the outlet, wherein the filter holder is configured such that the material to be extruded flows through the membrane filter assembly and into the outlet cavity via the plurality of passages before being discharged through the outlet.

Item 2 the filter holder of item 1, wherein the housing includes an upper housing portion, a lower housing portion, and a middle housing portion between the upper housing portion and the lower housing portion, and wherein the middle housing portion surrounds an outer periphery of the filter support member.

Item 3 the filter holder of item 2, wherein the downstream side includes a first recess, wherein the lower housing portion includes a second recess, and wherein the first recess and the second recess at least partially define the outlet cavity.

Item 4 the filter holder of item 3, wherein the upper housing portion includes a recess, wherein the recess and the filter support surface at least partially define an inlet cavity, and wherein the plurality of passages is in fluid communication with the inlet cavity.

Item 5 the filter holder of item 2, wherein the upper housing portion includes a recess, wherein the recess and the filter support surface at least partially define an inlet cavity, and wherein the plurality of passages is in fluid communication with the inlet cavity.

Item 6 the filter holder of item 1, wherein at least one of the plurality of passages extends parallel to a longitudinal center axis of the housing.

Item 7 the filter holder of any of items 2-5, wherein at least one of the plurality of passages extends parallel to a longitudinal center axis of the housing.

Item 8 the filter holder of item 1, wherein at least one of the plurality of passages extends at a non-zero angle relative to a longitudinal center axis of the housing.

Item 9 the filter holder of any of items 2-6, wherein at least one of the plurality of passages extends at a non-zero angle relative to a longitudinal center axis of the housing.

Item 10 the filter holder of item 1, wherein the filter support member includes a circumferential groove.

Item 11 the filter holder of any of items 2-6 or 8, wherein the filter support member includes a circumferential groove.

Item 12 the filter holder of item 11, further comprising a temperature regulating assembly configured to circulate a heat transfer fluid through the circumferential groove.

Item 13 the filter holder of item 10, further comprising a temperature regulating assembly configured to circulate a heat transfer fluid through the circumferential groove.

Item 14 the filter holder of item 1, wherein the membrane filter assembly includes a polycarbonate membrane having a pore size between 10 nanometers and 1 micrometer.

Item 15 the filter holder of any of items 2-6, 8, 10, or 13, wherein the membrane filter assembly includes a polycarbonate membrane having a pore size between 10 nanometers and 1 micrometer.

Item 16 the filter holder of item 1, wherein the downstream side includes a recess with a curved surface, and wherein the recess at least partially defines the outlet cavity.

Item 17 the filter holder of any of items 2-6, 8, 10, 13, or 14, wherein the downstream side includes a recess with a curved surface, and wherein the recess at least partially defines the outlet cavity.

Item 18 the filter holder of item 17, wherein the curved surface is hemispherical.

Item 19 the filter holder of item 16, wherein the curved surface is hemispherical.

Item 20 the filter holder of item 1, wherein the filter support member includes a plurality of interconnected channels formed in the downstream side of the filter support member.

Item 21 the filter holder of any of items 2-6, 8, 10, 13, or 14, wherein the filter support member includes a plurality of interconnected channels formed in the downstream side of the filter support member.

Item 22 the filter holder of item 1, wherein the filter support surface has a maximum width between 5 mm and 600 mm.

Item 23 the filter holder of item 1, wherein the filter support surface has a maximum width between 13 mm and 293 mm.

Item 24 a filter holder for liposome extrusion, the filter holder comprising:

a housing defining a longitudinal center axis, the housing including an inlet extending from an inlet cavity and an outlet extending from an outlet cavity; and a filter support member disposed within the housing between the inlet cavity and the outlet cavity, the filter support member including:

an upstream side adjacent the inlet cavity, the upstream side having a filter support surface configured to support a membrane filter assembly, a downstream side adjacent the outlet cavity and opposite the upstream side, and a plurality of passages extending through the filter support member from the upstream side to the downstream side, wherein the filter holder is configured such that the material to be extruded flows through the membrane filter assembly and into the outlet cavity via the plurality of passages before being discharged through the outlet.

Item 25 the filter holder of item 24, wherein the housing includes an upper housing portion, a lower housing portion, and a middle housing portion between the upper housing portion and the lower housing portion, and wherein the filter support member is disposed within the middle housing portion.

Item 26 the filter holder of item 25, wherein the lower housing portion includes a lower recess at least partially defining the outlet cavity, and wherein the upper housing portion includes an upper recess at least partially defining the inlet cavity.

Item 27 the filter holder of item 25, wherein the lower housing portion includes a lower recess, and wherein the downstream side of the filter support member is flat such that the lower recess defines the outlet cavity.

Item 28 the filter holder of item 24, wherein at least one of the plurality of passages extends at a non-zero angle relative to the longitudinal center axis. Item 29 the filter holder of any of items 25-27, wherein at least one of the plurality of passages extends at a non-zero angle relative to the longitudinal center axis.

Item 30 the filter holder of item 24, wherein the housing includes a recess, wherein the filter support member is received within the recess, and wherein the filter holder further comprises a spacer disposed between the downstream side of the filter support member and an opposing surface of the recess.

Item 31 the filter holder of item 25 or 28, wherein the housing includes a recess, wherein the filter support member is received within the recess, and wherein the filter holder further comprises a spacer disposed between the downstream side of the filter support member and an opposing surface of the recess.

Item 32 the filter holder of item 24, wherein the downstream side of the filter support member includes a concave recess at least partially defining the outlet cavity.

Item 33 the filter holder of any of items 25, 26, or 28, wherein the downstream side of the filter support member includes a concave recess at least partially defining the outlet cavity.

Item 34 an extrusion system comprising:
a supply reservoir containing material to be extruded;
a pressure source configured to pressurize material to be extruded drawn from the reservoir;
a filter holder including
a housing having an inlet configured to receive the pressurized material to be extruded and an outlet configured to discharge an extrudate,
a membrane filter assembly disposed between the inlet and the outlet,
a filter support member disposed within the housing, the filter support member including:
an upstream side having a filter support surface configured to support the membrane filter assembly,
a downstream side opposite the upstream side, the downstream side including a first recess, and
a plurality of passages extending through the filter support member from the filter support surface to the first recess, and
an outlet cavity at least partially defined by the first recess, the outlet cavity in fluid communication with the outlet; and
a collection reservoir configured to receive the extrudate from the outlet of the filter holder.

Item 35 the extrusion system of item 34, wherein the filter holder is one of a plurality of identical filter holders fluidly coupled to the supply reservoir and the collection reservoir in parallel.

Item 36 the extrusion system of item 34, wherein the filter holder is one of a plurality of identical filter holders fluidly coupled to the supply reservoir and the collection reservoir in series.

Item 37 the extrusion system of item 34, wherein one or more heat exchangers are included between the supply and collection reservoirs.

Item 38 the extrusion system of item 36 or 37, wherein one or more heat exchangers are included between the supply and collection reservoirs.

What is claimed is:

1. A filter holder for liposome extrusion, the filter holder comprising:
a housing including an inlet configured to receive a material to be extruded and an outlet;
a filter support member disposed within the housing between the inlet and the outlet, the filter support member including:
an upstream side having a filter support surface configured to support a membrane filter assembly,
a downstream side opposite the upstream side, and
a plurality of passages extending through the filter support member from the filter support surface to the downstream side; and
an outlet cavity in fluid communication with the outlet,
wherein the filter holder is configured such that the material to be extruded flows through the membrane filter assembly and into the outlet cavity via the plurality of passages before being discharged through the outlet; and
wherein the filter support member includes a plurality of interconnected channels formed in the downstream side of the filter support member.

2. The filter holder of claim 1, wherein the housing includes an upper housing portion, a lower housing portion, and a middle housing portion between the upper housing portion and the lower housing portion, and wherein the middle housing portion surrounds an outer periphery of the filter support member.

3. The filter holder of claim 2, wherein the downstream side includes a first recess, wherein the lower housing portion includes a second recess, and wherein the first recess and the second recess at least partially define the outlet cavity.

4. The filter holder of claim 2, wherein the upper housing portion includes a recess, wherein the recess and the filter support surface at least partially define an inlet cavity, and wherein the plurality of passages is in fluid communication with the inlet cavity.

5. The filter holder of claim 1, wherein
i) at least one of the plurality of passages extends parallel to a longitudinal center axis of the housing; and/or
ii) wherein at least one of the plurality of passages extends at a non-zero angle relative to a longitudinal center axis of the housing.

6. The filter holder of claim 1, wherein the membrane filter assembly includes a polycarbonate membrane having a pore size between 10 nanometers and 1 micrometer.

7. The filter holder of claim 1, wherein the downstream side includes a recess with a curved surface, and wherein the recess at least partially defines the outlet cavity.

8. The filter holder of claim 7, wherein the curved surface is hemispherical.

9. The filter holder of claim 1, wherein the filter support surface has a maximum width between 5 mm and 600 mm or between 13 mm and 293 mm.

10. A filter holder for liposome extrusion, the filter holder comprising:
a housing defining a longitudinal center axis, the housing including an inlet extending from an inlet cavity and an outlet extending from an outlet cavity; and
a filter support member disposed within the housing between the inlet cavity and the outlet cavity, the filter support member including:
an upstream side adjacent the inlet cavity, the upstream side having a filter support surface configured to support a membrane filter assembly,
a downstream side adjacent the outlet cavity and opposite the upstream side, and
a plurality of passages extending through the filter support member from the upstream side to the downstream side, wherein the filter holder is configured such that the material to be extruded flows through the membrane filter assembly and into the outlet cavity via the plurality of passages before being discharged through the outlet; and wherein the filter support member includes a plurality of interconnected channels formed in the downstream side of the filter support member.

11. The filter holder of claim 10, wherein the housing includes an upper housing portion, a lower housing portion, and a middle housing portion between the upper housing portion and the lower housing portion, and wherein the filter support member is disposed within the middle housing portion.

12. The filter holder of claim 11, wherein the lower housing portion includes a lower recess at least partially defining the outlet cavity, and wherein the upper housing portion includes an upper recess at least partially defining the inlet cavity.

13. The filter holder of claim 11, wherein the lower housing portion includes a lower recess, and wherein the downstream side of the filter support member is flat such that the lower recess defines the outlet cavity.

14. The filter holder of claim 10, wherein at least one of the plurality of passages extends at a non-zero angle relative to the longitudinal center axis.

15. The filter holder of claim 10, wherein the housing includes a recess, wherein the filter support member is received within the recess, and wherein the filter holder further comprises a spacer disposed between the downstream side of the filter support member and an opposing surface of the recess.

16. The filter holder of claim 10, wherein the downstream side of the filter support member includes a concave recess at least partially defining the outlet cavity.

17. An extrusion system comprising:

a supply reservoir containing material to be extruded;

a pressure source configured to pressurize material to be extruded drawn from the reservoir;

a filter holder including a housing having an inlet configured to receive the pressurized material to be extruded and an outlet configured to discharge an extrudate, a membrane filter assembly disposed between the inlet and the outlet, a filter support member disposed within the housing, the filter support member including:

an upstream side having a filter support surface configured to support the membrane filter assembly, a downstream side opposite the upstream side, the downstream side including a first recess, and a plurality of passages extending through the filter support member from the filter support surface to the first recess, and an outlet cavity at least partially defined by the first recess, the outlet cavity in fluid communication with the outlet; and a collection reservoir configured to receive the extrudate from the outlet of the filter holder; and wherein the filter support member includes a plurality of interconnected channels formed in the downstream side of the filter support member.

18. The extrusion system of claim 17, wherein the filter holder is one of a plurality of identical filter holders fluidly coupled to the supply reservoir and the collection reservoir i) in parallel; or ii) in series.

19. The extrusion system of claim 17, wherein one or more heat exchangers are included between the supply and collection reservoirs.

20. A filter holder for liposome extrusion, the filter holder comprising:

a housing including an inlet configured to receive a material to be extruded and an outlet;

a filter support member disposed within the housing between the inlet and the outlet, the filter support member including:

an upstream side having a filter support surface configured to support a membrane filter assembly, a downstream side opposite the upstream side, and a plurality of passages extending through the filter support member from the filter support surface to the downstream side; and an outlet cavity in fluid communication with the outlet, wherein the filter holder is configured such that the material to be extruded flows through the membrane filter assembly and into the outlet cavity via the plurality of passages before being discharged through the outlet;

wherein the filter support member includes a circumferential groove; and wherein the filter holder further comprises a temperature regulating assembly configured to circulate a heat transfer fluid through the circumferential groove.

21. A filter holder for liposome extrusion, the filter holder comprising:

a housing defining a longitudinal center axis, the housing including an inlet extending from an inlet cavity and an outlet extending from an outlet cavity; and a filter support member disposed within the housing between the inlet cavity and the outlet cavity, the filter support member including:

an upstream side adjacent the inlet cavity, the upstream side having a filter support surface configured to support a membrane filter assembly, a downstream side adjacent the outlet cavity and opposite the upstream side, and a plurality of passages extending through the filter support member from the upstream side to the downstream side, wherein the filter holder is configured such that the material to be extruded flows through the membrane filter assembly and into the outlet cavity via the plurality of passages before being discharged through the outlet;

wherein the filter support member includes a circumferential groove; and wherein the filter holder further comprises a temperature regulating assembly configured to circulate a heat transfer fluid through the circumferential groove.

* * * * *